United States Patent
Farmer et al.

(10) Patent No.: US 10,252,969 B2
(45) Date of Patent: Apr. 9, 2019

(54) METHODS FOR PRODUCTION OF AROMATIC DICARBOXYLIC ACIDS AND DERIVATIVES THEREOF

(71) Applicant: Novomer, Inc., Waltham, MA (US)

(72) Inventors: Jay J Farmer, Ithaca, NY (US); Sadesh H. Sookraj, Cambridge, MA (US)

(73) Assignee: Novomer, Inc., Boston, MA (US)

( * ) Notice: Subject to any disclaimer, the term of this patent is extended or adjusted under 35 U.S.C. 154(b) by 0 days.

(21) Appl. No.: 15/809,612

(22) PCT Filed: Apr. 22, 2016

(86) PCT No.: PCT/US2016/029020
§ 371 (c)(1),
(2) Date: Nov. 10, 2017

(87) PCT Pub. No.: WO2016/172609
PCT Pub. Date: Oct. 27, 2016

(65) Prior Publication Data
US 2018/0105480 A1    Apr. 19, 2018

Related U.S. Application Data

(60) Provisional application No. 62/187,326, filed on Jul. 1, 2015, provisional application No. 62/151,589, filed on Apr. 23, 2015.

(51) Int. Cl.
| | | |
|---|---|---|
| C07C 63/16 | (2006.01) | |
| C07C 63/24 | (2006.01) | |
| C07C 63/26 | (2006.01) | |
| C07C 67/34 | (2006.01) | |
| C07C 67/39 | (2006.01) | |
| C07C 69/80 | (2006.01) | |
| C07C 69/82 | (2006.01) | |

(Continued)

(52) U.S. Cl.
CPC .......... *C07C 51/235* (2013.01); *C07C 51/353* (2013.01); *C07C 63/16* (2013.01); *C07C 63/24* (2013.01); *C07C 63/26* (2013.01); *C07C 67/34* (2013.01); *C07C 67/39* (2013.01); *C07C 69/82* (2013.01); *C07D 493/08* (2013.01)

(58) Field of Classification Search
None
See application file for complete search history.

(56) References Cited

U.S. PATENT DOCUMENTS

| | | | |
|---|---|---|---|
| 6,677,464 B2 | 1/2004 | Kuwayama et al. | |
| 2017/0002136 A1* | 1/2017 | Sookraj | C08G 63/183 |

FOREIGN PATENT DOCUMENTS

| | | |
|---|---|---|
| WO | WO 2014/144843 | 9/2014 |
| WO | WO 2014/197195 | 12/2014 |

OTHER PUBLICATIONS

Gresham ("Beta-propiolactone. XV. Use in the Diene Synthesis" J. Am. Chem. Soc. 1954, vol. 76 p. 609) (Year: 1954).*

(Continued)

*Primary Examiner* — Amy C Bonaparte
(74) *Attorney, Agent, or Firm* — McCracken & Gillen LLC

(57) ABSTRACT

Provided are methods for the production of isophthalic acid (IPA) and derivatives thereof. The methods are based on the addition of beta propiolactone to furfural or a derivative thereof. Provided are cost effective routes to biobased IPA and derivatives thereof, including terephthalic acid.

9 Claims, 4 Drawing Sheets

(51) Int. Cl.
*C07C 51/235* (2006.01)
*C07C 51/353* (2006.01)
*C07D 493/08* (2006.01)

(56) References Cited

OTHER PUBLICATIONS

International Search Report and Written Opinion dated Jul. 25, 2016, for International Application No. PCT/US2016/029020, Applicant Novomer, Inc. (23 pages).

Tachibana et al., Synthesis and Verification of Biobased Terephthalic Acid from Furfural, Scientific Reports 5, Article No. 8249, 2015 (Published online: Feb. 4, 2015) (5 pages).

Pacheco et al. Synthesis of Terephthalic Acid via Diels-Alder Reactions with Ethylene and Oxidized Variants of 5-Hydroxymethylfurfural, Proceedings of the National Academy of Sciences, 111(23), dated May 7, 2014 (5 pages).

\* cited by examiner

METHODS FOR PRODUCTION OF AROMATIC DICARBOXYLIC ACIDS AND DERIVATIVES THEREOF

CROSS-REFERENCE TO RELATED APPLICATIONS

This application claims priority to U.S. Provisional Patent Application Nos. 62/151,589, filed Apr. 23, 2015, and 62/187,326, filed Jul. 1, 2015, and PCT Application No. PCT/US16/029020, filed Apr. 22, 2016 which are incorporated herein by reference in their entireties.

FIELD

The present disclosure relates generally to the production of aromatic dicarboxylic acid compounds and derivatives thereof, and more specifically to the production of phthalic acid (PA), isophthalic acid (IP A), and terephthalic acid (TP A) and their esters and derivatives.

BACKGROUND

Phthalic acid (PA), Isophthalic acid (IP A), and Terephthalic acid (TP A) and their esters and derivatives are important precursors for the synthesis of polyesters and other useful materials.

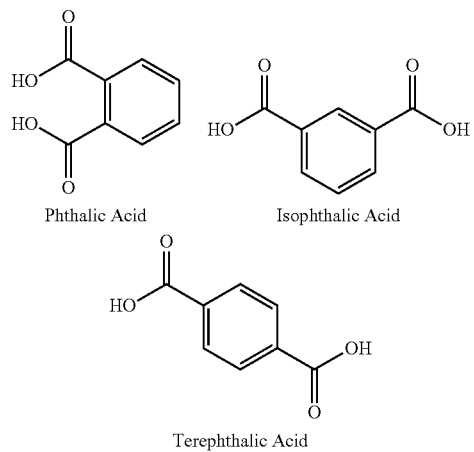

Phthalic Acid    Isophthalic Acid

Terephthalic Acid

The largest use of IP A and TP A at present is production of high performance polyamide and polyester polymers. For example, TPA is used to produce polyethylene terephthalate (PET) which is used extensively in consumer goods packaging, most prominently in the now ubiquitous clear plastic water bottles. IP A is also used to make polyesters as well as high performance polyamides. PA is an important precursor to plasticizers used in a range of polymers. Together PA, IP A, and TPA are produced on the scale of many millions of tons per year scale by oxidation of xylenes which are obtained from petroleum distillates.

There is strong demand from consumers and consumer goods companies for sustainable alternatives to petroleum-based plastics for packaging applications. Indeed, Coca Cola® and others have recently introduced PET containing biobased monoethylene glycol (MEG). Beverage bottles made from this PET are branded as the "Plant Bottle™" and have been well received in the marketplace. Unfortunately, since about 70% of the mass (and 8 out of every 10 carbon atoms) in PET derives from terephthalic and isophthalic acids, replacing petroleum-sourced MEG with biobased material yields PET that is only about 30% biobased. There is huge interest in biobased IP A and TPA to enable fully biobased PET production, but to date no economically feasible biobased processes exist.

BRIEF SUMMARY

In one aspect, provided are methods for producing phthalic acid (PA) and isophthalic acid (IP A) and derivatives thereof. In some embodiments, the methods are based on the reaction of beta propiolactone (BPL) with furfural or a derivative thereof to provide a cyclohexene intermediate as shown in the general scheme below. Furfural derivatives may include, for example, furfural compounds with a protected aldehyde, such as the acetal compounds described herein.

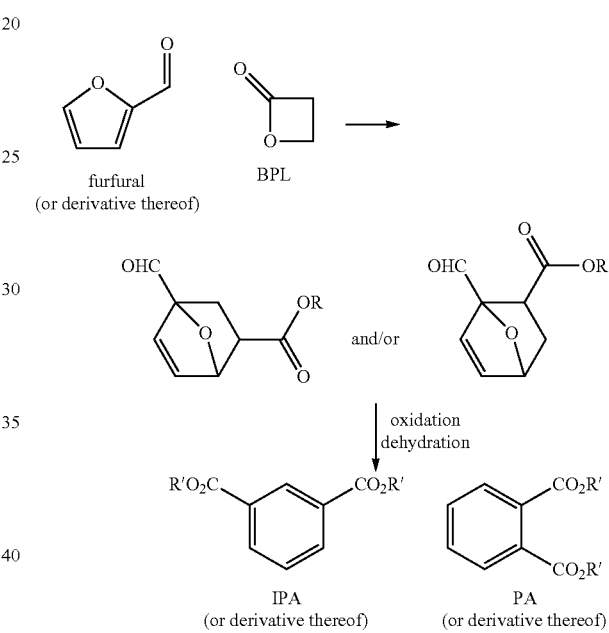

The resulting adducts have all eight carbon atoms connected as needed for PA and IPA production. Oxidation and dehydration of the adducts (either tandemly or in a series of operations) provides phthalic and/or isophthalic acid (or esters or other derivatives thereof). Since furfural is already produced on the scale of millions of tons per year from biobased feedstocks, the methods described herein provide an efficient and practical way to make biobased PA and IP A. Additionally, the methods described herein provide attractive new routes to biobased TP A.

The renewable content of the diacids produced can be further increased by utilizing a biobased alpha beta unsaturated carboxylic acid. For example, the renewable content of the diacids produced can be further increased by utilizing biobased BPL. BPL can be obtained by carbonylation of ethylene oxide, which in turn is readily available from bio-sourced ethanol. As such, the present methods provide a practical and cost-effective route to 100% renewable IPA and TP A.

In another aspect, provided are processes for producing PA and/or IPA based on the reaction of furfural (or derivatives thereof) with BPL. In certain embodiments, the methods described herein operate in a continuous flow format. In certain embodiments, the methods include continuously passing a mixture of furfural (or a derivative thereof) and beta propiolactone through a heated reaction zone, optionally in the presence of solvent, catalysts, or co-reactants.

In certain embodiments, subsequent oxidation of the addition product of furfural with the BPL is performed in a continuous flow format. In certain embodiments, two or more reactions selected from the group consisting of: dehydration to remove the bridgehead oxygen, dehydration of the cyclohexene ring to an aryl ring, oxidation of the aldehyde to a carboxylic acid, and esterification or saponification of one or both carboxyl groups of the final product occur without isolation of intermediate products. In certain embodiments, cycloaddition of the furfural (or a derivative thereof) and BPL occurs in a first fixed bed reactor and the effluent from the reactor is fed to a second reactor where the product is heated under dehydrative conditions to effect aromatization of the addition product.

In another aspect, provided are processes for producing PA and/or IP A that are integrated with an ethylene oxide-based process for BPL production. In certain embodiments, the ethylene oxide-based process produces BPL continuously and a stream from that process is fed to a continuous reactor where it is contacted with furfural. In certain embodiments, the resulting product is fed to an aromatization reactor where it is converted to an aromatic diacid (or mixture of diacids). In certain embodiments, the process includes a rearrangement reactor for conversion to phthalic acid and/or isophthalic acid to terephthalic acid.

In certain embodiments, provided are integrated processes for the production of phthalic and/or isophthalic and/or terephthalic acids from ethylene oxide and furfural, one or both of which may be biobased:

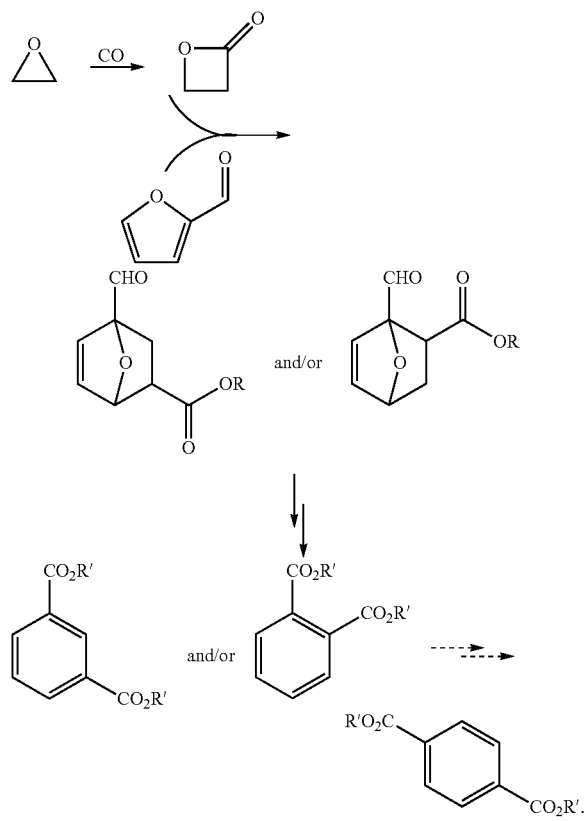

In another aspect, provided are compounds having the formula:

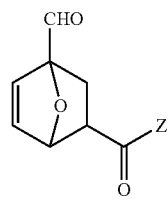

wherein Z is as defined below and described in the classes and subclasses herein.

In a further aspect, provided are aromatic diacid compositions. In certain embodiments, provided are isophthalic and/or terephthalic acid compositions characterized in that they contain or are derived from IP A that is produced by cycloaddition of an alpha-beta unsaturated acid or ester to furfural or a derivative thereof. In certain embodiments, the aromatic diacid compositions are characterized in that five of the eight carbon atoms in the IPA (and/or TPA) are derived from biobased furfural. In certain embodiments, provided aromatic diacid compositions are characterized in that three of the eight carbon atoms in the IPA (and/or TPA) are derived from a biobased alpha beta unsaturated acid (or a derivative of such a biobased acid). In certain embodiments where the alpha beta unsaturated acid is derived from ethylene oxide and carbon monoxide, one, two or three of the carbon atoms in the alpha beta unsaturated acid may be derived from biobased feedstocks. By extension, aromatic diacid compositions provided herein may contain various degrees of bio content: for example only one biobased carbon atom (e.g. bio CO is combined with fossil-based EO to produce acrylic acid which is combined with non-biobased furfural), two biobased carbon atoms (e.g. biobased ethylene oxide is combined with fossil-based CO to make acrylic acid which is combined with non-biosourced furfural), three biobased carbon atoms (e.g., biobased acrylic acid is combined with non-biosourced furfural), five biobased carbon atoms (bio furfural is combined with fossil-derived acrylic acid), six biobased carbon atoms (bio furfural is combined with acrylic acid derived from biosourced CO and fossil-derived EO), seven biobased carbon atoms (e.g. bio furfural is combined with acrylic acid derived from biosourced EO and fossil-derived CO), or eight biobased carbon atoms (bio furfural plus bio acrylic acid). This is a unique property of the processes described herein and enables an IPA (and/or TPA) producer to offer customers a range of price points and bio-content. In a related aspect, provided are PET compositions with varying biocontent derivable by combining the IPA and/or TPA compositions described with biosourced or fossil-based monoethylene glycol (MEG).

In another aspect, provided are processes for producing IP A based on the cycloaddition of furfural (or derivatives thereof) with acrylic acid (or derivatives thereof). In certain embodiments, the processes operate in a continuous flow format. In certain embodiments, the process includes continuously passing a mixture of furfural (or a derivative thereof) and an alpha beta unsaturated acid over a bed of solid catalyst where the catalyst promotes the Diels Alder cycloaddition reaction of these two chemicals. In certain embodiments, the oxidation of the cycloaddition product of furfural with the alpha beta unsaturated acid is performed in a continuous flow format. In certain embodiments, two or more reactions selected from the group consisting of: dehydration to remove the bridgehead oxygen, dehydration of the cyclohexene ring to an aryl ring, oxidation of the aldehyde to a carboxylic acid, and esterification or saponification of one or both carboxyl groups of the final product occur without isolation of intermediate products. In certain embodiments, cycloaddition of the furfural and alpha beta unsaturated acid (or derivative) occurs in a first fixed bed reactor (the Diels Alder reactor) and the effluent from the Diels Alder reactor is fed to a second reactor where the product is heated under oxidative conditions to effect aromatization of the cycloaddition product.

In another aspect, provided are processes for producing IPA that are integrated with an ethylene oxide-based process for acrylic acid production. In certain embodiments, the ethylene oxide-based process produces beta propiolactone (BPL) as an intermediate. In certain embodiments, the resulting isophthalic acid is further converted to terephthalic acid. In certain embodiments, the conversion to terephthalic acid is a continuous process fed from the continuous oxidative aromatization reactor.

In certain embodiments, provided are integrated processes for the production of isophthalic and/or terephthalic acid from ethylene oxide and furfural, one or both of which may be biobased:

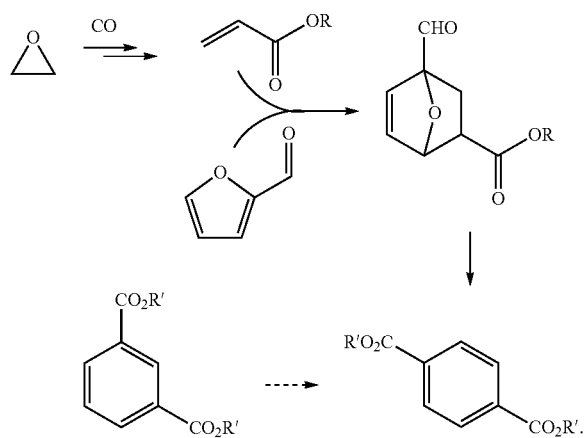

BRIEF DESCRIPTION OF THE FIGURES

The present application can be best understood by reference to the following description taken in conjunction with the accompanying figures, in which like parts may be referred to by like numerals.

DEFINITIONS

Figure 1:
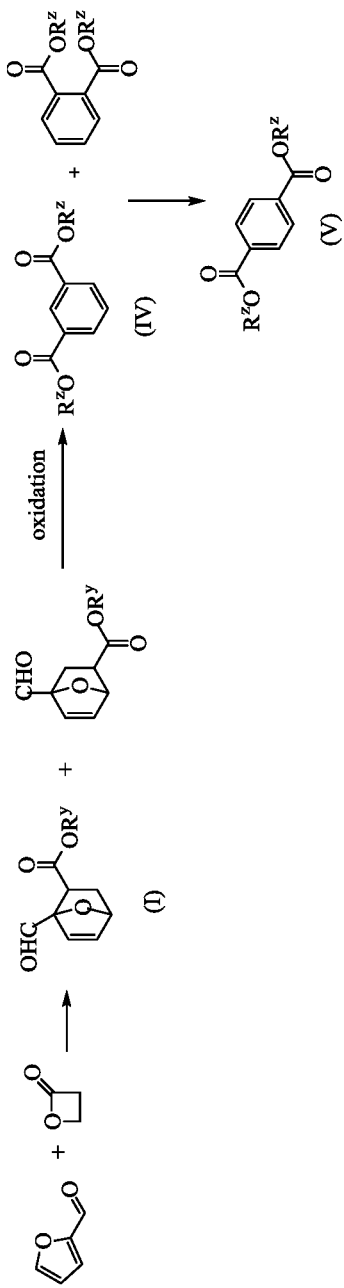
FIG. 1 depicts an exemplary process to produce compounds of Formulae IV and V from furfural and beta propiolactone.

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987.

Certain compounds described herein can comprise one or more asymmetric centers, and thus can exist in various stereoisomeric forms, e.g., enantiomers and/or diastereomers. Thus, compounds and compositions thereof may be in the form of an individual enantiomer, diastereomer or geometric isomer, or may be in the form of a mixture of stereoisomers. In certain embodiments, the compounds described herein are enantiopure compounds. In certain other embodiments, mixtures of enantiomers or diastereomers are provided.

Furthermore, certain compounds as described herein may have one or more double bonds that can exist as either a Z or E isomer, unless otherwise indicated. In some variation, the compounds are individual isomers substantially free of other isomers and alternatively, as mixtures of various isomers, e.g., racemic mixtures of enantiomers. In addition to the above-mentioned compounds per se, provided are compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the description herein. For instance, a compound may, in some embodiments, be provided substantially free of one or more corresponding stereoisomers, and may also be referred to as "stereochemically enriched".

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments, the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In some variations, the aliphatic group is unbranched or branched. In other variations, the aliphatic group is cyclic. Unless otherwise specified, in some variations, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments, aliphatic groups contain 1-2 carbon atoms. Suitable aliphatic groups include, for example, linear or branched, alkyl, alkenyl, and alkynyl groups, and hybrids thereof such as (cycloalkyl) alkyl, (cycloalkenyl)alkyl or (cycloalkyl)alkenyl.

The term "heteroaliphatic", as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups. In some variations, the heteroaliphatic group is branched or unbranched. In other variations, the heteroaliphatic group is cyclic. In yet other variations, the heteroaliphatic group is acyclic.

The term "epoxide", as used herein, refers to a substituted or unsubstituted oxirane. Substituted oxiranes include, for example, monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "glycidyl", as used herein, refers to an oxirane substituted with a hydroxyl methyl group or a derivative thereof. The term glycidyl as used herein includes moieties having additional substitution on one or more of the carbon atoms of the oxirane ring or on the methylene group of the hydroxymethyl moiety, such substitution may include, for example, alkyl groups, halogen atoms, and aryl groups. The terms glycidyl ester, glycidyl acrylate, glycidyl ether etc. denote substitution at the oxygen atom of the above-mentioned hydroxymethyl group, i.e. that oxygen atom is bonded to an acyl group, an acrylate group, or an alkyl group, respectively.

The term "acrylate" or "acrylates", as used herein, refers to any acyl group having a vinyl group adjacent to the acyl carbonyl. The terms encompass mono-, di- and tri-substituted vinyl groups. Acrylates may include, for example, acrylate, methacrylate, ethacrylate, cinnamate (3-phenylacrylate), crotonate, tiglate, and senecioate.

The term "polymer", as used herein, refers to a molecule comprising multiple repeating units. In some variations, the polymer is a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, the polymer is a copolymer, terpolymer, heteropolymer, block copolymer, or tapered heteropolymer of one or more epoxides. In one variation, the polymer may be a copolymer, terpolymer, heteropolymer, block copolymer, or tapered heteropolymer of two or more monomers.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, for example, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl", as used herein, refers to a saturated hydrocarbon radical. In some variations, the alkyl group is a saturated, straight- or branched-chain hydrocarbon radicals derived from an aliphatic moiety containing between one and six carbon atoms by removal of a single hydrogen atom. Unless otherwise specified, in some variations, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments, alkyl groups contain 1-3 carbon atoms, and in yet other embodiments alkyl groups contain 1-2 carbon atoms. Alkyl radicals may include, for example, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, and dodecyl.

The term "alkenyl", as used herein, denotes a monovalent group having at least one carbon-carbon double bond. In some variations, the alkenyl group is a monovalent group derived from a straight- or branched-chain aliphatic moiety having at least one carbon-carbon double bond by the removal of a single hydrogen atom. Unless otherwise specified, in some variations, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, and I-methyl-2-buten-I-yl.

The term "alkynyl", as used herein, refers to a monovalent group having at least one carbon-carbon triple bond. In some variations, the alkynyl group is a monovalent group derived from a straight- or branched-chain aliphatic moiety having at least one carbon-carbon triple bond by the removal of a single hydrogen atom. Unless otherwise specified, in some variations, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, for example, ethynyl, 2-propynyl (propargyl), and 1-propynyl.

The term "carbocycle" and "carbocyclic ring", as used herein, refer to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include, for example, cyclopropane, cyclobutane, cyclopentane, cyclohexane, bicyclo[2,2,1]heptane, norbornene, phenyl, cyclohexene, naphthalene, and spiro[4.5]decane.

The term "aryl", used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments, "aryl" refers to an aromatic ring system which includes, for example, phenyl, naphthyl, and anthracyl, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, and tetrahydronaphthyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 pi (π) electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and may be saturated or partially unsaturated, and have, in addition to carbon atoms, one or more, preferably one to four, heteroatoms, as defined above. In some variations, the heterocyclic group is a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, for example, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds described herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —(CH$_2$)$_{0-4}$R°; —(CH$_2$)$_{0-4}$ OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-4}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$CH$_2$)$_{0-2}$C(O)OR$^\bullet$, —(CH$_2$)$_{0-4}$C(O)N(R°)$_2$; —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$-Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^\dagger$, —NR$^{\dagger 2}$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger_2$, —C(S)NR$^\dagger_2$, —C(NH)NR$^{\dagger 2}$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

As used herein, the term "about" preceding one or more numerical values means the numerical value ±5%. It should be understood that reference to "about" a value or parameter herein includes (and describes) embodiments that are directed to that value or parameter per se. For example, description referring to "about x" includes description of "x" per se.

DETAILED DESCRIPTION

Compositions of Matter

In some aspects, provided are compositions comprising compounds of Formula I:

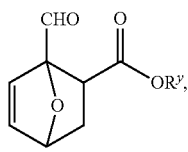

(I)

wherein $R^Y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group.

In certain embodiments, provided are substantially pure compounds of Formula I. In certain embodiments, provided are reaction mixtures or process streams comprising compounds of Formula I.

In certain embodiments, provided are compositions comprising the compound of Formula I, wherein $R^Y$ is —H. In certain embodiments, provided are compositions comprising a compound of Formula I, wherein $R^Y$ is $C_{1-20}$ aliphatic, or where $R^Y$ is $C_{1-12}$ aliphatic, or where $R^Y$ is $C_{1-8}$ aliphatic, or where $R^Y$ is $C_{1-6}$ aliphatic, or where $R^Y$ is $C_{1-4}$ aliphatic. In certain embodiments, provided are compositions comprising the compound of Formula I, wherein $R^Y$ is selected from the group consisting of methyl, ethyl, propyl, n-butyl, and 2-ethylhexyl.

In certain embodiments, provided is a compound selected from the group consisting of:

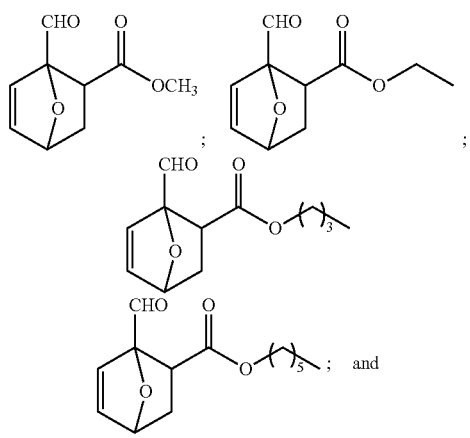

-continued

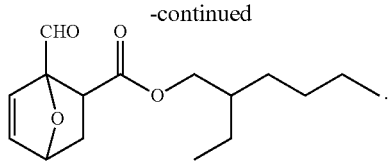

In certain aspects, provided are compositions comprising compounds of Formula I':

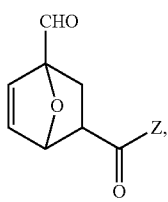

(I')

wherein Z is selected from the group consisting of —$OR^y$, —Cl, —Br, —$NR^y_2$, and —$SR^y$, wherein each $R^y$ is independently hydrogen, or an optionally substituted group selected the group consisting of: acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; or wherein two $R^y$ on a nitrogen atom may be taken with the nitrogen atom to form an optionally substituted 4- to 7-membered heterocyclic ring having 0-2 additional heteroatoms independently selected from the group consisting of nitrogen, oxygen, and sulfur.

In certain embodiments, provided are substantially pure compounds of Formula I'. In certain embodiments, provided are reaction mixtures or process streams comprising compounds of Formula I'.

In some variations, Z is —$OR^y$. In one variation, $R^y$ is —H, and Z is —OH. Thus, in certain embodiments, provided are compositions comprising the compound of Formula I', wherein Z is —OH. In certain embodiments, provided are compositions comprising a compound of Formula I', wherein Z is —$OR^y$ and $R^y$ is $C_{1-20}$ aliphatic, or where $R^y$ is $C_{1-12}$ aliphatic, or where $R^y$ is $C_{1-8}$ aliphatic, or where $R^y$ is $C_{1-6}$ aliphatic, or where $R^y$ is $C_{1-4}$ aliphatic. In certain embodiments, provided are compositions comprising the compound of Formula I', wherein Z is —$OR^y$ and $R^y$ is selected from the group consisting of methyl, ethyl, propyl, n-butyl, and 2-ethylhexyl.

In certain embodiments, provided is a compound selected from the group consisting of:

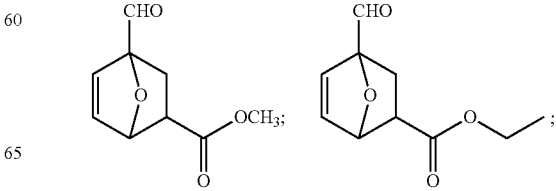

15

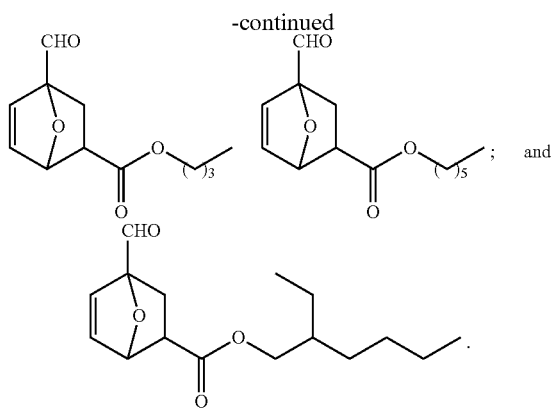

In some variations, Z is —NR$^y$$_2$. In one variation, the two R$^y$ may be taken with the nitrogen atom to which they are attached to form an optionally substituted 4- to 7 membered heterocyclic ring having 0-2 additional heteroatoms independently selected from the group consisting of nitrogen, oxygen, and sulfur.

In other variations, Z is —SR$^y$.

In certain embodiments, provided are compositions comprising compounds of Formula II:

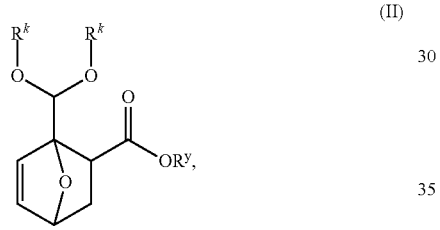

(II)

wherein R$^Y$ is as defined above and in the classes and subclasses herein, and R$^k$ is, independently at each occurrence, selected from the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two R$^k$ may be taken with intervening atoms to form an optionally substituted 4- to 7-membered heterocyclic ring having 0-2 additional heteroatoms independently selected from the group consisting of nitrogen, oxygen, and sulfur.

In certain embodiments, provided are substantially pure compounds of Formula II. In certain embodiments, provided are reaction mixtures or process streams comprising compounds of Formula II.

In certain embodiments, provided is a composition comprising compounds of Formula II, wherein R$^y$ is —H. In certain embodiments, provided are compositions comprising a compound of Formula II, wherein R$^y$ is C$_{1-20}$ aliphatic, or where R$^y$ is C$_{1-12}$ aliphatic, or where R$^y$ is C$_{1-8}$ aliphatic, or where R$^y$ is C$_{1-6}$ aliphatic, or where R$^y$ is C$_{1-4}$ aliphatic. In certain embodiments, provided are compositions comprising the compound of Formula II, wherein R$^Y$ is selected from the group consisting of methyl, ethyl, propyl, n-butyl, and 2-ethylhexyl.

16

In certain embodiments, provided are compositions comprising one or more compounds selected from the group consisting of:

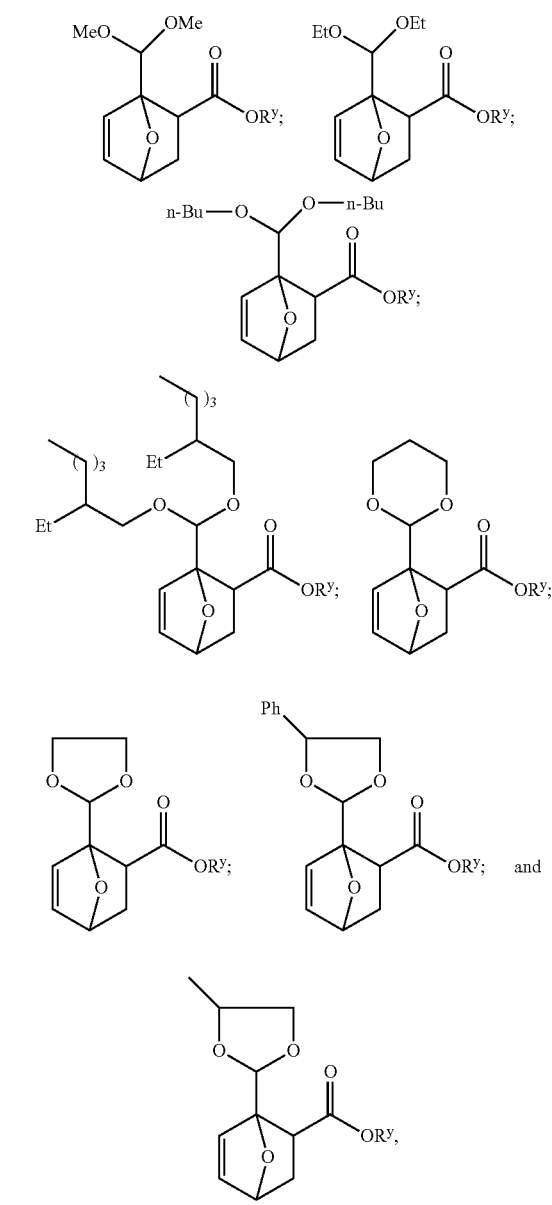

where R$^y$ is as defined above and in the classes and subclasses herein.

In certain embodiments, for compounds of Formula II, each R$^k$ is the same as R$^y$. In certain embodiments, provided is a compound selected from the group consisting of:

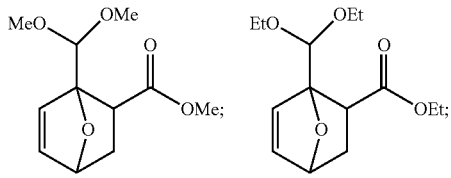

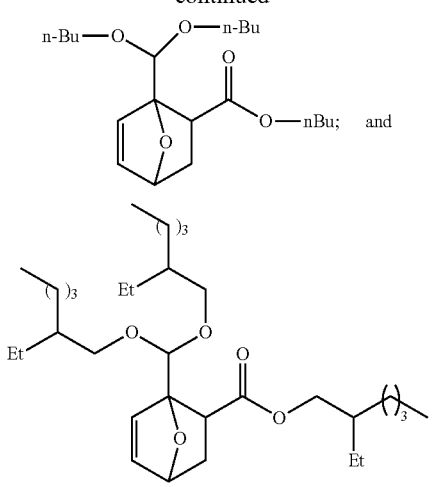

In some variations, provided are compositions comprising compounds of Formula II':

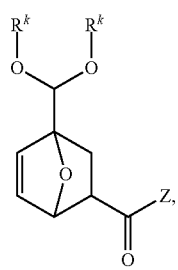

(II')

wherein each of $R^k$ and Z is as defined above and in the classes and subclasses herein.

In certain embodiments, provided are substantially pure compounds of Formula II'. In certain embodiments, provided are reaction mixtures or process streams comprising compounds of Formula II'.

In certain embodiments, the invention encompasses a compound selected from the group consisting of:

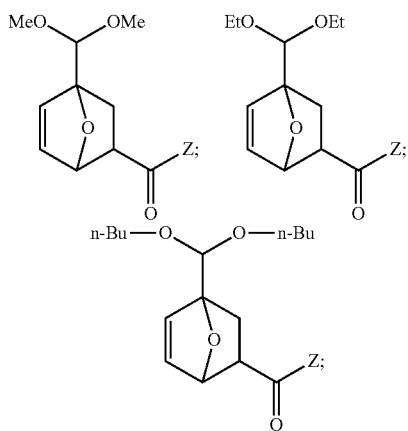

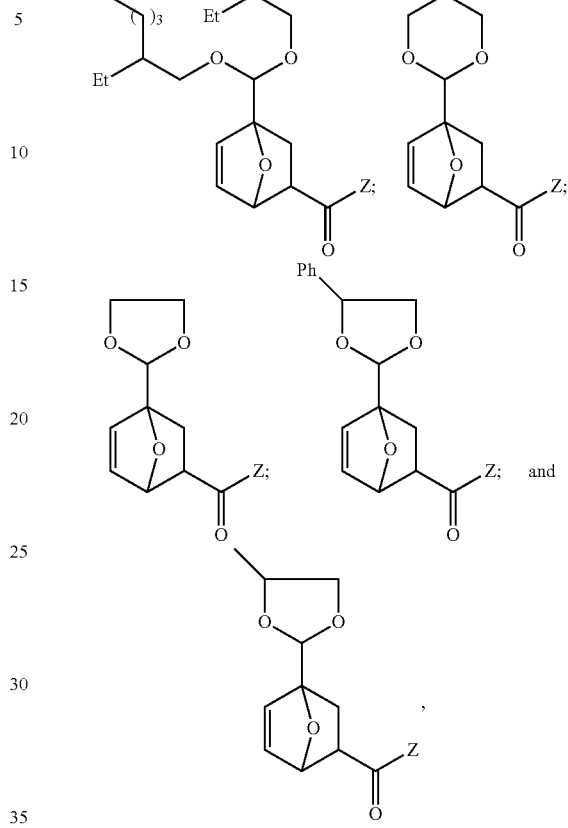

wherein Z is as defined above and in the classes and subclasses herein.

In certain embodiments, provided is a composition comprising compounds of Formula II', wherein Z is —$OR^y$. In certain embodiments, provided is a composition comprising compounds of Formula II', wherein Z is —OH. In certain embodiments, provided compositions comprising a compound of Formula II', wherein Z is —$OR^y$ and $R^y$ is $C_{1-20}$ aliphatic, or where $R^y$ is $C_{1-12}$ aliphatic, or where $R^y$ is $C_{1-5}$ aliphatic, or where $R^y$ is $C_{1-6}$ aliphatic, or where $R^y$ is $C_{1-4}$ aliphatic. In certain embodiments, provided are compositions comprising the compound of Formula II', wherein Z is —$OR^y$ and $R^y$ is selected from the group consisting of methyl, ethyl, propyl, n-butyl, and 2-ethylhexyl.

In certain embodiments, for compounds of Formula II', Z is —$OR^y$ and each of $R^k$ is the same as $R^y$. In certain embodiments, the invention encompasses a compound selected from a group consisting of:

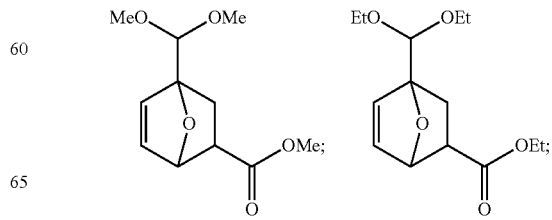

-continued

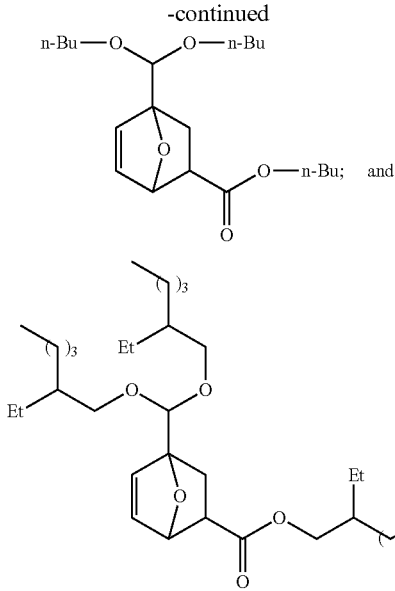

In certain embodiments, provided are mixtures comprising compounds of Formula II and compounds of Formula IIb:

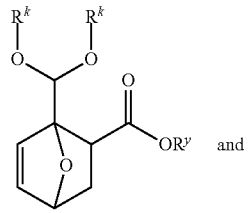

II

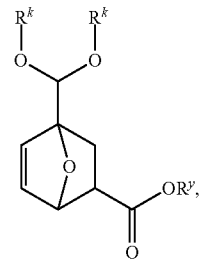

IIb wherein each of $R^y$ and $R^k$ is as defined above and in the classes and subclasses herein.

In certain embodiments, provided are compositions comprising a mixture of compounds having the formula:

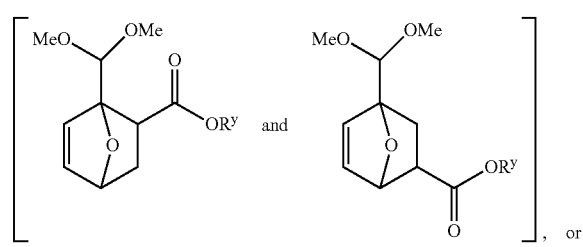

-continued

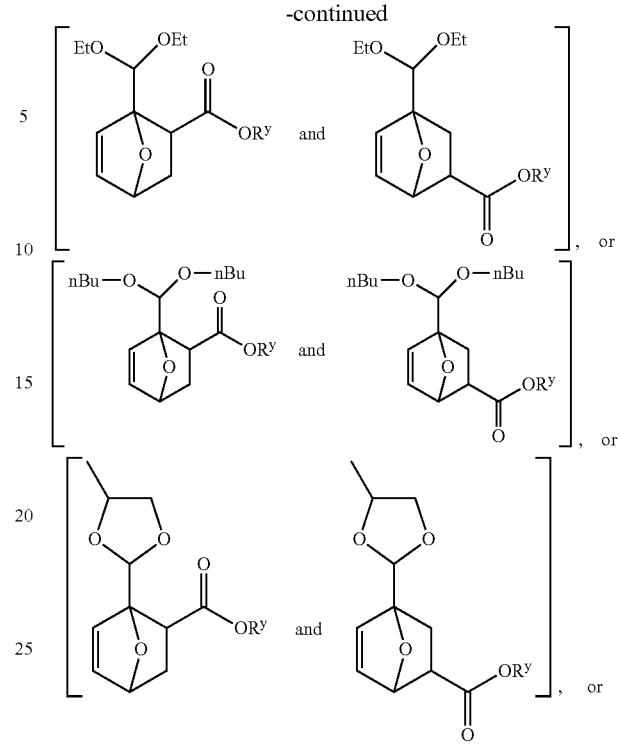

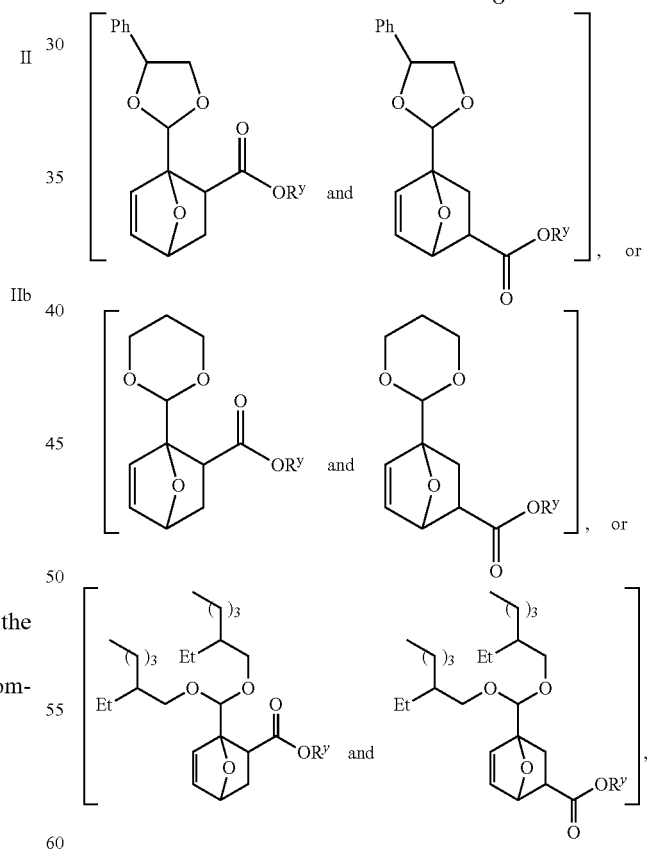

wherein $R^y$ is as defined above and in the classes and subclasses herein.

In certain embodiments, for the mixtures of compounds of Formulae II and IIb, each $R^k$ and $R^y$ is the same. In certain embodiments, provided are compositions containing mixtures of compounds having the formulae:

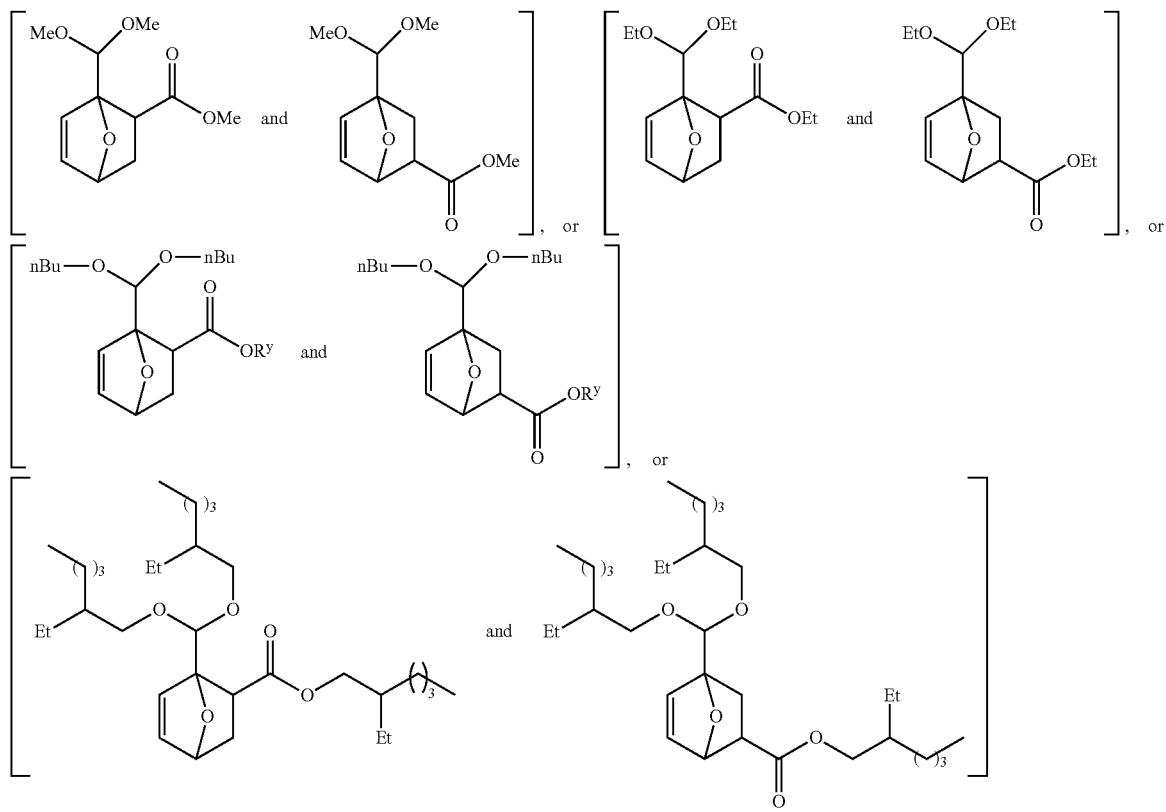

In certain embodiments, provided are compositions comprising compounds of Formula III:

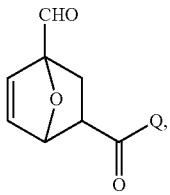
(III)

wherein Q is a solid support.

In certain embodiments, 0 comprises an inorganic support. In certain embodiments, Q comprises an organic resin. In certain embodiments, the linkage to the solid support Q comprises an ester bond. In certain embodiments, the linkage to the solid support comprises an amide bond.

In certain embodiments, provided are compositions comprising compounds of Formula IIIa:

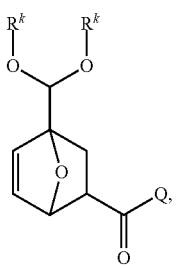
(IIIa)

wherein each of Q and $R^k$ is as defined above and in the classes and subclasses herein.

In certain embodiments, provided are compositions comprising compounds of

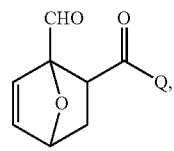

wherein Q is as defined above and in the classes and subclasses herein.

In certain embodiments, provided are compositions comprising compounds of formula:

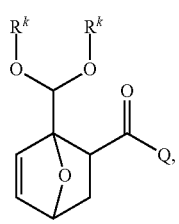

wherein each of Q and $R^k$ is as defined above and in the classes and subclasses herein.

Methods and Making

In some aspects, provided herein are various methods to produce phthalic acid, isophthalic acid, and terephthalic acid, and esters and derivatives thereof In some embodiments, provided are methods to produce isophthalic acid and terephthalic acid, and esters and derivatives thereof, from (i) furfural and (ii) beta propiolactone or an alpha beta unsaturated acid (or an ester, amide or thioester of such an unsaturated acid).

Figure 3A:
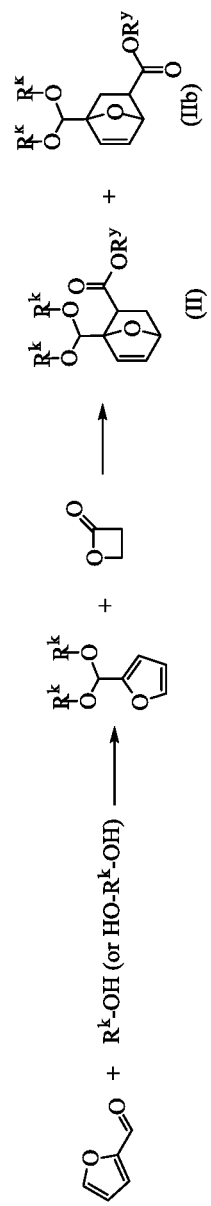
FIG. 3A depicts an exemplary process to produce compounds of Formulae II and IIb from furfural and an alcohol.

For example, with reference to FIG. 1, an exemplary pathway is depicted to produce compounds of Formula IV, which may include isophthalic acid, and compounds of Formula V, which may include terephthalic acid, from furfural and beta propiolactone. In some variations, as depicted in FIG. 3A, furfural and beta propiolactone may combined to produce acetal compounds. In certain variations, such acetal compounds may be hydrolyzed and oxidized to produce compounds of Formula IV, which may include isophthalic acid. The compounds of Formula IV may be isolated. In other variations, the compounds of Formula IV may rearrange under suitable conditions to produce compounds of Formula V, which may include terephthalic acid.

Figure 2A:
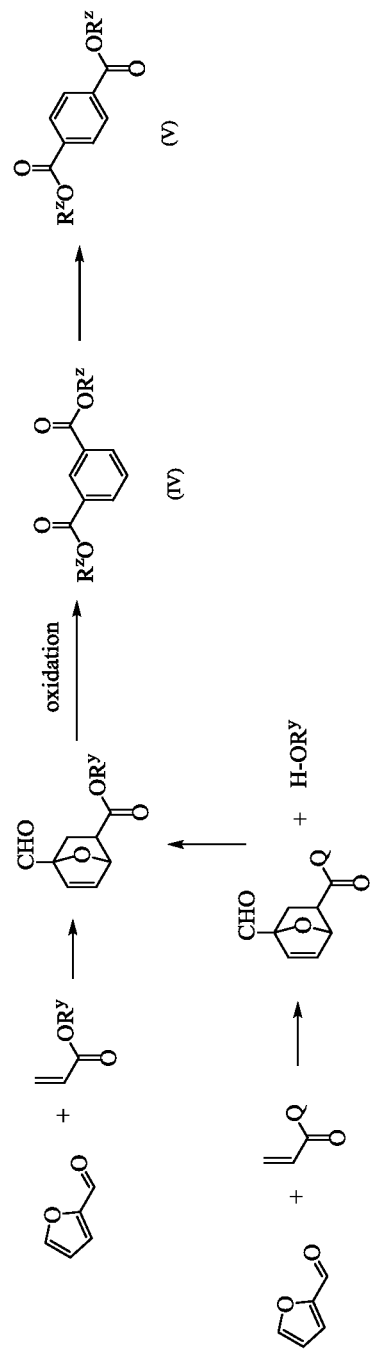
FIG. 2A depicts exemplary process to produce compounds of Formulae IV and V from furfural and alpha beta unsaturated acids.
Figure 3B:
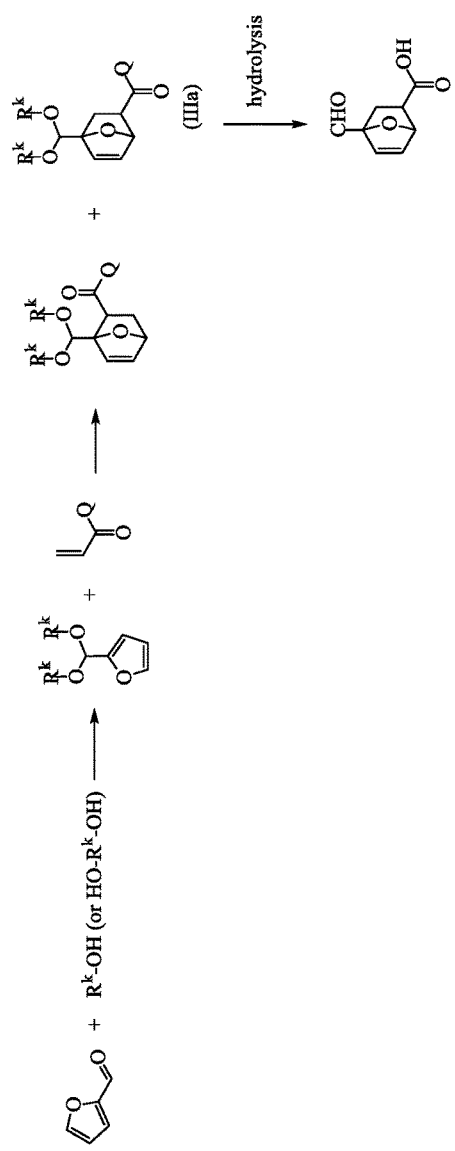
FIG. 3B depicts an exemplary process to produce 4-formyl-7oxabicyclo[2.2.1]hept-5-ene-2-carboxylic acid from furfural and an alcohol.

With reference to FIG. 2A, an exemplary pathway is depicted to produce compounds of Formula IV, which may include isophthalic acid, and compounds of Formula V, which may include terephthalic acid, from furfural and an alpha beta unsaturated acid or an ester thereof. In some variations, as depicted in FIG. 3B, acetal compounds may be produced from furfural and the alpha beta unsaturated acid or ester thereof in certain variations, such acetal compounds may be oxidized to produce compounds of Formula IV, which may include isophthalic acid. The compounds of Formula IV may be isolated. In other variations, the compounds of Formula IV may rearrange under suitable conditions to produce compounds of Formula V, which may include terephthalic acid.

Figure 2B:
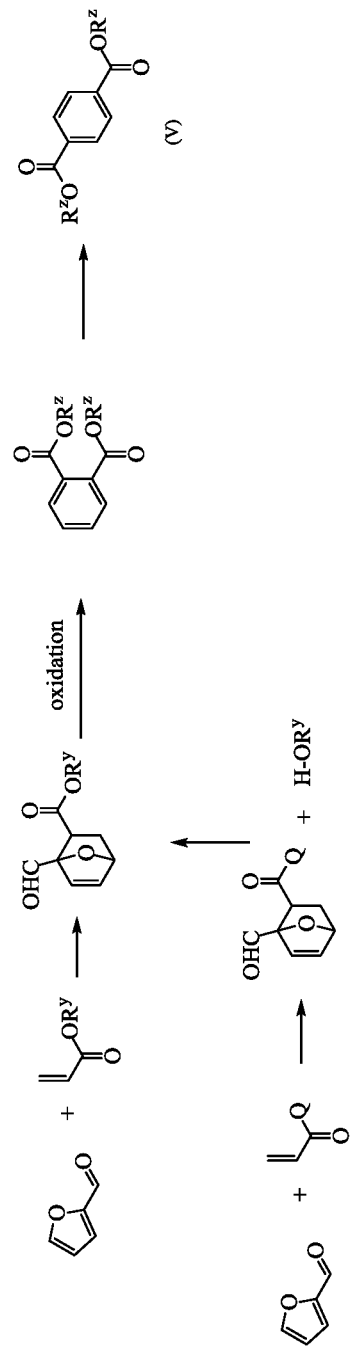
FIG. 2B depicts exemplary process to produce compounds of Formula V from furfural and alpha beta unsaturated acids.

With reference to FIG. 2B, an exemplary pathway is depicted to produce phthalic acid or esters thereof, and compounds of Formula V, which may include terephthalic acid, from furfural and an alpha beta unsaturated acid or an ester thereof. In some variations, as depicted in FIG. 3B, acetal compounds may be produced from furfural and the alpha beta unsaturated acid or ester thereof. In certain variations, such acetal compounds may be oxidized to produce phthalic acid or esters thereof. The phthalic acid or esters may be isolated. In other variations, the phthalic acid or esters may rearrange under suitable conditions to produce compounds of Formula V, which may include terephthalic acid.

In other aspects, provided herein are methods to produce acetal compounds. Such acetal compounds may, in certain variations, be used to produce phthalic acid, isophthalic acid, and terephthalic acid, and esters and derivatives thereof.

Figure 3C:
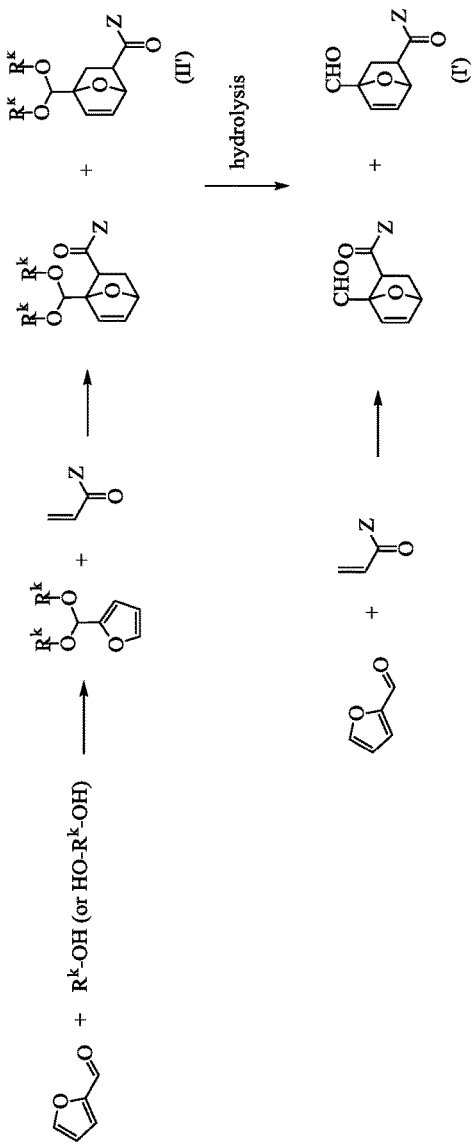
FIG. 3C depicts an exemplary processes to produce a compound of Formula I' from furfural.

For example, with reference to FIGS. 3A-3C, exemplary pathways are depicted to produce various acetal compounds from furfural and an alcohol of formula $R^kOH$ or $OH—R^k—OH$. With reference to FIGS. 3B and 3C, the acetal compounds may undergo hydrolysis to produce compounds that may be further oxidized to produce compounds of Formula IV, which may include isophthalic acid, and compounds of Formula V, which may include terephthalic acid (as depicted in FIGS. 1 and 2).

Figure 4A:
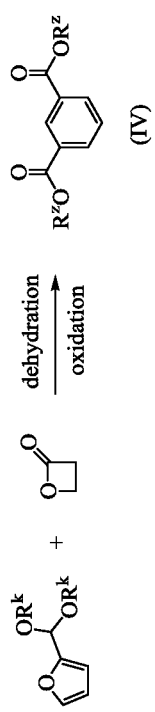
FIG. 4A depicts an exemplary process to produce a compound of Formula IV from an acetal compound and beta propiolactone.
Figure 4B:
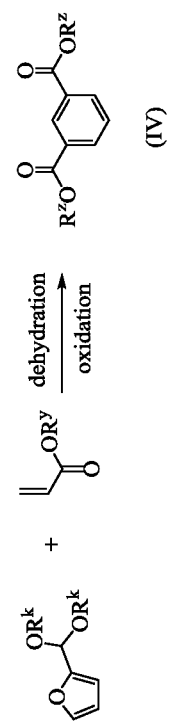
FIG. 4B depicts an exemplary process to produce a compound of Formula IV from an acetal compound and an alpha beta unsaturated acid or ester.

With reference again to FIGS. 3A-3C, the acetal compounds from furfural and an alcohol of formula $R^k—OH$ of $OH—R^k—OH$ may be used in other reactions to produce compounds of Formulae IV and V. For example, in one variation, with reference to FIG. 4A, the acetal compound may be combined with beta propiolactone, and the product may undergo dehydration and oxidation to produce compounds of Formula IV. In another variation, with reference to FIG. 4B, the acetal compound may be combined with an alpha beta unsaturated acid or ester, and the product may undergo dehydration and oxidation to produce compounds of Formula IV. In other variations, the compounds of Formula IV may rearrange under suitable conditions to produce compounds of Formula V.

The various methods to make compounds of Formula IV and V, along with various acetal compounds, are described in further detail below.

The reaction of furfural (or acetals thereof) with BPL, alpha beta unsaturated acids or alpha beta unsaturated acid derivatives (such as esters, amides and thioesters) can, in principal produce two regioisomeric products wherein either: the aldehyde (or acetal) carbon atom of furfural and the carboxylic carbon atom from the BPL or alpha beta unsaturated acid (or derivative thereof) are situated on adjacent carbon atoms of the cyclohexene ring of the product, or wherein the carboxylic carbon atom from the BPL or alpha beta unsaturated acid (or derivative thereof) are situated with unsubstituted ring carbon separating them (as shown in FIG. 3A). Such isomers may be shown separately in the methods described below, but it is to be understood that mixtures of the two regioisomers may also be formed and that such isomeric mixtures may be separated to isolate a desired isomer. Such regioisomeric mixtures may also be carried on as a mixture to one or more subsequent steps. All such variations are contemplated herein though all variations may not be explicitly shown in the schemes and descriptions that follow.

Methods Based on Addition of BPL to Furfural

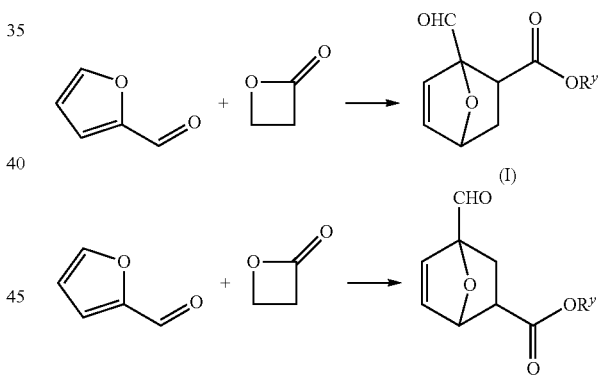

In certain aspects provided are methods that utilize BPL and furfural as starting materials.

In certain aspects, provided are methods of making compounds including adducts of BPL and furfural, as well as aromatized and oxidized products of such adducts including aromatic dicarboxylic acids.

In some embodiments, provided are methods of making a compound of Formula I:

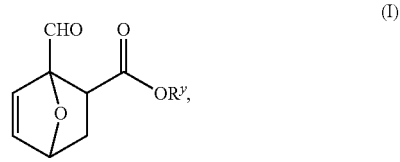

the method comprising reacting furfural with beta propiolactone, and optionally an alcohol of formula HOR$^y$ wherein R$^y$ is hydrogen, or an optionally substituted moiety selected the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 14 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In some variations of the foregoing, when the alcohol of formula HOR$^y$ is absent, then R$^y$ is H with respect to the compound of Formula I.

In certain embodiments, provided are methods of making a compound of Formula I:

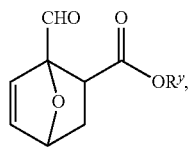

(I)

the method comprising reacting furfural with beta propiolactone, where R$^y$ is as defined above and in the classes and subclasses herein.

In certain embodiments, the methods include reacting furfural with beta propiolactone in the presence of an alcohol. In certain embodiments where the reaction is conducted in the presence of an alcohol, the resulting product is an ester of that alcohol (e.g., the alcohol is the form HO—R$^y$ where R$^y$ is other than —H).

In certain embodiments, where the method comprises reacting furfural and beta propiolactone in the presence of an alcohol of formula HOR$^y$, R$^y$ is C$_{1-20}$ aliphatic, or C$_{1-12}$ aliphatic, or C$_{1-5}$ aliphatic, or C$_{1-6}$ aliphatic, or C$_{1-4}$ aliphatic. In certain embodiments, R$^y$ is selected from the group consisting of methyl, ethyl, n-butyl, and 2-ethylhexyl.

In certain embodiments, the reacting of furfural with the beta propiolactone comprises heating a mixture of the furfural and the beta propiolactone. In certain embodiments, the mixture is heated to a temperature between 50° C. and 300° C. In certain embodiments, the mixture is heated to a temperature between 50° C. and 150° C., between 100° C. and 200° C., between 120° C. and 180° C. or between 150° C. and 220° C. In certain embodiments, heating of the mixture of the furfural and the beta propiolactone comprises flowing the mixture through a heated plug flow reactor.

In certain embodiments, the reacting of furfural with the beta propiolactone comprises contacting a mixture of the two substances with a catalyst. In certain embodiments, the catalyst is a Diels Alder catalyst. In certain embodiments, the catalyst is a Lewis acidic catalyst.

In some embodiments, provided are methods of making a compound of Formula:

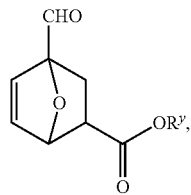

the method comprising reacting furfural with beta propiolactone, and optionally an alcohol of formula HOR$^y$, wherein R$^y$ is hydrogen, or an optionally substituted moiety selected the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In some variations of the foregoing, when the alcohol of formula HOR$^y$ is absent, then R$^y$ is H with respect to the compound of Formula:

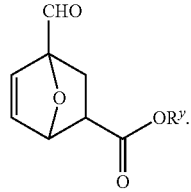

In certain embodiments, the methods include reacting furfural with beta propiolactone in the presence of an alcohol. In certain embodiments where the reaction is conducted in the presence of an alcohol, the resulting product is an ester of that alcohol (e.g. the alcohol is the form HO—R$^y$ where R$^y$ is other than —H.)

In certain embodiments, where the method comprises reacting furfural and beta propiolactone in the presence of an alcohol of formula HOR$^y$ is C$_{1-20}$ aliphatic, or C$_{1-12}$ aliphatic, or C$_{1-8}$ aliphatic, or C$_{1-6}$ aliphatic, or C$_{1-4}$ aliphatic. In certain embodiments, R$^y$ is selected from the group consisting of methyl, ethyl, n-butyl, and 2-ethylhexyl.

In certain embodiments, the reacting of furfural with the beta propiolactone comprises heating a mixture of the furfural and the beta propiolactone. In certain embodiments, the mixture is heated to a temperature between 50° C. and 300° C. In certain embodiments, the mixture is heated to a temperature between 50° C. and 150° C., between 100° C. and 200° C., between 120° C. and 180° C. or between 150° C. and 220° C. In certain embodiments, heating of the mixture of the furfural and the beta propiolactone comprises flowing the mixture through a heated plug flow reactor.

In certain embodiments, the reacting of furfural with the beta propiolactone comprises contacting a mixture of the two substances with a catalyst. In certain embodiments, the catalyst is a Diels Alder catalyst. In certain embodiments, the catalyst is a Lewis acidic catalyst.

Methods Based on Adducts of BPL with Acetals of Furfural

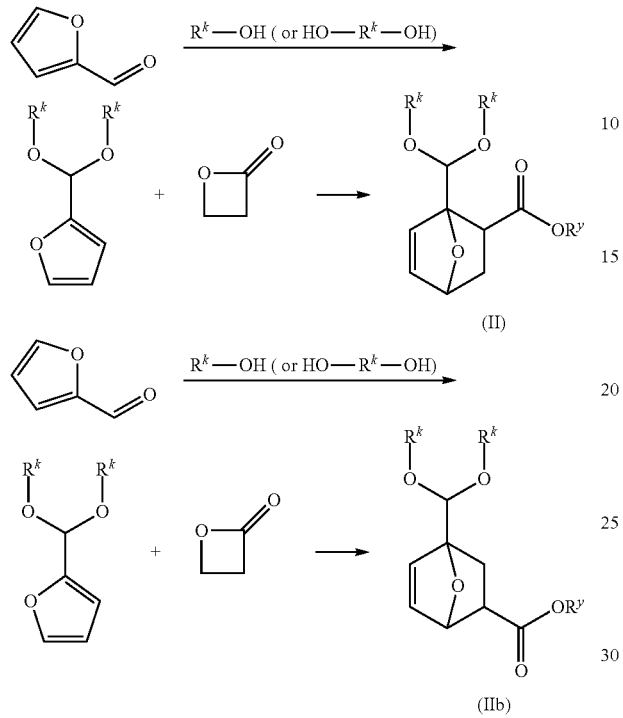

(II)

(IIb)

In certain aspects provided are methods that utilize BPL and acetals of furfural as starting materials. In certain aspects, provided are methods of making compounds including adducts of BPL and furfural acetals, as well as aromatized and oxidized products of such adducts including aromatic dicarboxylic acids. In some embodiments, provided are methods of making compounds of Formula IIb:

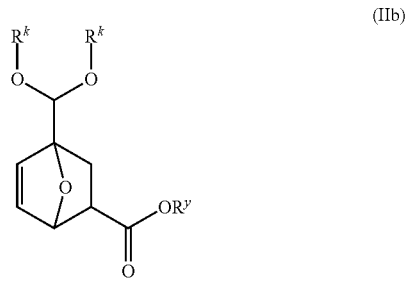

(IIb)

the method comprising:
a) reacting furfural with an alcohol of formula $R^k$—OH (or HO—$R^k$—OH) under dehydrating conditions to provide an acetal compound of formula:

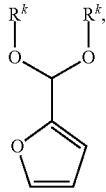

and b) contacting the acetal with beta propiolactone, and optionally an alcohol of formula HOR$^y$, to produce the compounds of Formula IIb, wherein:

$R^k$ is, independently at each occurrence, selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two $R^k$ may be taken with intervening atoms to form an optionally substituted 4- to 7-membered heterocyclic ring having 0-2 additional heteroatoms independently selected from the group consisting of nitrogen, oxygen, and sulfur, and $R^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In some variations of the foregoing, when the alcohol of formula HOR$^y$ is absent, then $R^y$ is H with respect to the compound of Formula IIb.

In certain embodiments, where the method comprises reacting the acetal and beta propiolactone in the presence of an alcohol of formula HOR$^y$R$^y$ is $C_{1-20}$ aliphatic, or $C_{1-12}$ aliphatic, or $C_{1-8}$ aliphatic, or $C_{1-6}$ aliphatic, or $C_{1-4}$ aliphatic. In certain embodiments, $R^y$ is selected from the group consisting of methyl, ethyl, n-butyl, and 2-ethylhexyl.

In certain embodiments provided are methods of making compounds of Formula IIb:

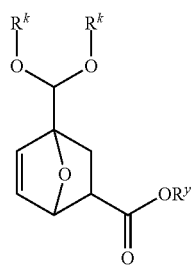

(IIb)

the method comprising:
a) reacting furfural with an alcohol of formula $R^k$—OH (or HO—$R^k$—OH) under dehydrating conditions to provide an acetal compound of formula:

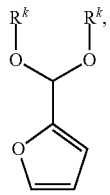

and
b) contacting the acetal with beta propiolactone, wherein each of $R^k$ and $R^y$ are as defined above and in the classes and subclasses herein.

In some embodiments, provided are methods of making compounds of Formula II:

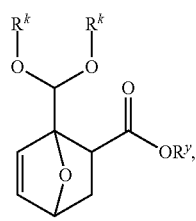

(II)

the method comprising:
a) reacting furfural with an alcohol of formula $R^k$—OH (or HO—$R^k$—OH) under dehydrating conditions to provide an acetal compound of formula:

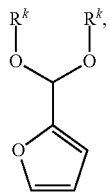

and
b) contacting the acetal with beta propiolactone, and optionally an alcohol of formula HOR$^y$, to produce the compounds of Formula II, wherein:
$R^k$ is, independently at each occurrence, selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two $R^k$ may be taken with intervening atoms to form an optionally substituted 4- to 7-membered heterocyclic ring having 0-2 additional heteroatoms independently selected from the group consisting of nitrogen, oxygen, and sulfur, and
$R^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In some variations of the foregoing, when the alcohol of formula HOR$^y$ is absent, then $R^y$ is H with respect to the compound of Formula II.

In certain embodiments, where the method comprises reacting the acetal and beta propiolactone in the presence of an alcohol of formula HOR$^y$R$^y$ is $C_{1-20}$ aliphatic, or $C_{1-12}$ aliphatic, or $C_{1-8}$ aliphatic, or $C_{1-6}$ aliphatic, or $C_{1-4}$ aliphatic. In certain embodiments, $R^y$ is selected from the group consisting of methyl, ethyl, n-butyl, and 2-ethylhexyl.

In certain embodiments provided are methods of making compounds of Formula II:

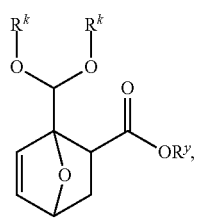

(II)

the method comprising:
a) reacting furfural with an alcohol of formula $R^k$—OH (or HO—$R^k$—OH) under dehydrating conditions to provide an acetal compound of formula:

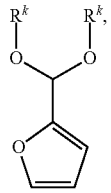

and
b) contacting the acetal with beta propiolactone, wherein each of $R^k$ and $R^y$ are as defined above and in the classes and subclasses herein.

In certain embodiments, the forming of the acetal and the contacting with beta propiolactone are performed concomitantly. In certain embodiments, the method comprises treating furfural and beta propiolactone under dehydrating conditions in the presence of an alcohol of formula $R^k$—OH (or HO—$R^k$—OH).

In certain embodiments, provided are methods for making compounds of Formulae II and/or IIb, wherein each $R^k$ is the same as $R^y$. In certain embodiments, such methods comprise the step of contacting beta propiolactone and furfural under dehydrating conditions in the presence of an alcohol of formula HOR$^k$:

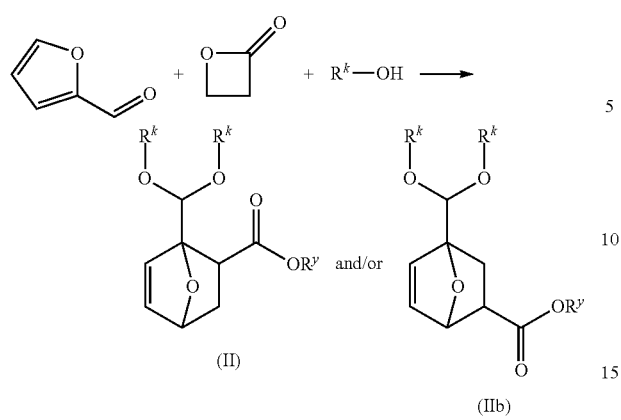

In certain embodiments the method comprises reacting the furfural and beta propiolactone in the presence of an alcohol of formula $HOR^y$, wherein $R^y$ is $C_{1-20}$ aliphatic, or $C_{1-12}$ aliphatic, or $C_{1-8}$ aliphatic, or $C_{1-6}$ aliphatic, or $C_{1-4}$ aliphatic. In certain embodiments, the method comprises reacting the furfural and beta propiolactone in the presence of an alcohol of formula $HOR^y$, wherein $R^y$ is selected from the group consisting of methyl, ethyl, n-butyl, and 2-ethylhexyl.

In some variations, provided are methods of making compounds of Formula II:

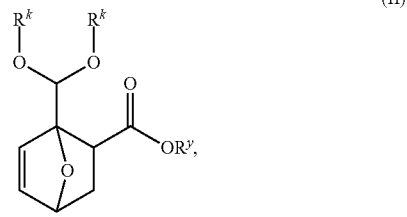

the method comprising:
a) reacting furfural with an alcohol of formula $R^k$—OH (or HO—$R^k$—OH) under dehydrating conditions to provide an acetal compound of formula:

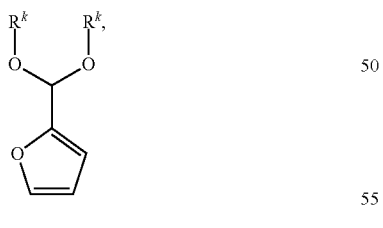

and
b) contacting the acetal with beta propiolactone, and optionally an alcohol of formula $HOR^y$, to produce the compounds of Formula II, wherein:
$R^k$ is, independently at each occurrence, selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two $R^k$ may be taken with intervening atoms to form an optionally substituted 4- to 7-membered heterocyclic ring having 0-2 additional heteroatoms independently selected from the group consisting of nitrogen, oxygen, and sulfur, and $R^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In one variation of the foregoing, when the alcohol of formula $HOR^y$ is absent, then $R^y$ is H with respect to the compound of Formula II.

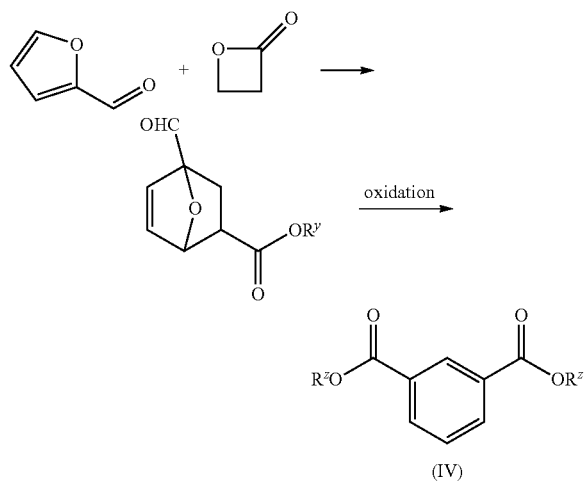

In some embodiments, provided are methods of making a compound of Formula IV:

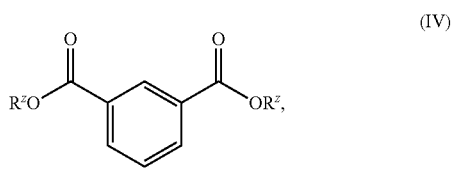

the method comprising contacting furfural with BPL, and oxidizing the resulting product, wherein $R^z$ is independently —H, $R^y$, optionally substituted $C_{1-20}$ aliphatic, or optionally substituted aryl.

In certain embodiments, provided are methods of making a compound of Formula IV:

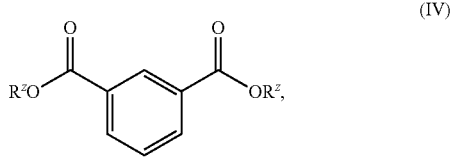

the method comprising contacting furfural with BPL and oxidizing and dehydrating the resulting product, where $R^z$ is as defined above and in the classes and subclasses herein.

In certain embodiments of the provided methods of making compounds of Formula IV, $R^z$ is —H (e.g. compound of Formula IV is isophthalic acid). Where $R^z$ is —H, the hydrogen atom may derive from any proton source present during the dehydration or oxidation processes. Such proton sources may include, for example, water, alcohols, organic acids, or mineral acids.

In certain embodiments of the provided methods of making compounds of Formula IV, $R^z$ is optionally substituted $C_{1-20}$ aliphatic or optionally substituted aryl. Where $R^z$ is alkyl or aryl it may derive from an aliphatic or aromatic alcohol present in the dehydration or oxidation steps.

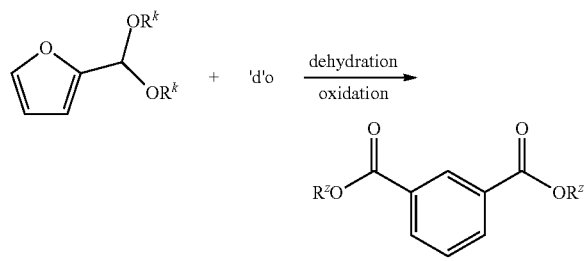

In some embodiments, provided are methods of making a compound of Formula IV:

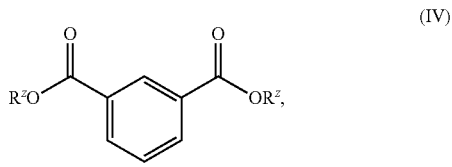

wherein $R^z$ is, independently at each occurrence, —H, $R^y$, optionally substituted $C_{1-20}$ aliphatic, or optionally substituted aryl, the method comprising contacting a compound of formula:

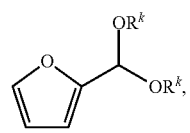

wherein $R^k$ is, independently at each occurrence, selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two $R^k$ may be taken with intervening atoms to form an optionally substituted 4- to 7-membered heterocyclic ring having 0-2 additional heteroatoms independently selected from the group consisting of nitrogen, oxygen, and sulfur, with BPL, and dehydrating and oxidizing the resulting product to produce the compound of Formula IV.

In certain embodiments, provided are methods of making a compound of Formula IV:

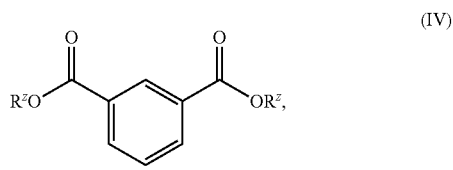

the method comprising contacting a compound of formula:

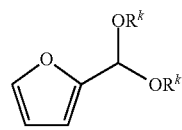

with BPL and hydrolyzing, dehydrating and oxidizing the resulting product, wherein each of $R^k$ and $R^z$ is as defined above and in the classes and subclasses herein.

In certain embodiments of the above methods of making compounds of Formula IV, $R^z$ is —H (e.g. compound IV is isophthalic acid). Where $R^z$ is —H, the hydrogen atom may derive from any proton source present during the dehydration or oxidation processes. Such proton sources may include for example, water, alcohols, organic acids, or mineral acids.

In certain embodiments of methods of making compounds of Formula IV, $R^z$ is optionally substituted $C_{1-20}$ aliphatic or optionally substituted aryl. Where R is alkyl or aryl it may derive from an aliphatic or aromatic alcohol present in the dehydration or oxidation steps.

Methods Based on Diels Alder Adducts of Furfural and Furfural Acetals

In another aspect, provided are methods of making compounds including Diels Alder adducts, aromatized analogs thereof, and aromatic dicarboxylic acids.

In certain aspects the provided methods utilize alpha beta unsaturated acids (or their esters, amides or thioesters) and furfural as starting materials to make aromatic diacids (or intermediates suitable for making such diacids). In certain aspects, provided are methods of making compounds including adducts of acrylic acid or its esters and furfural, as well as aromatized and oxidized products of such adducts including aromatic dicarboxylic acids.

In certain embodiments, provided methods conform to the following scheme:

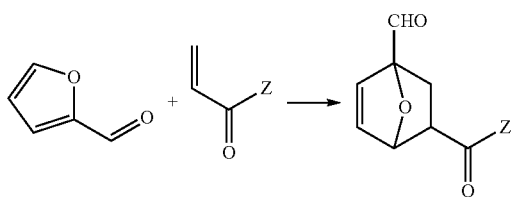 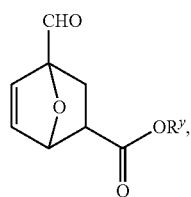

wherein Z is selected from the group consisting of —OR$^y$, —Cl, —Br, —NR$^y_2$, and —SR$^y$, wherein each R$^y$ is independently hydrogen, or an optionally substituted group selected the group consisting of: acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; or wherein two R$^y$ on a nitrogen atom may be taken with the nitrogen atom to form an optionally substituted 4- to 7-membered heterocyclic ring having 0-2 additional heteroatoms independently selected from the group consisting of nitrogen, oxygen, and sulfur.

In certain embodiments, Z is OR$^y$ and provided are methods depicted in the following scheme:

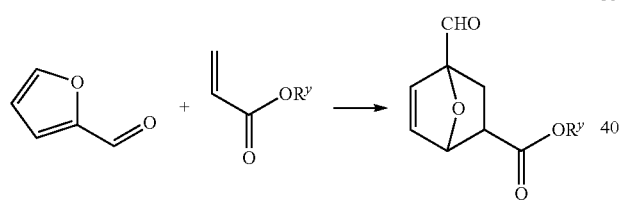

wherein R$^y$ is as defined above and in the classes and subclasses herein.

In certain embodiments, provided are methods of making a compound of formula:

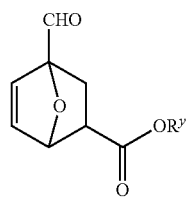

the method comprising reacting furfural with an alpha beta unsaturated acid or ester, wherein R$^y$ is as defined above and in the classes and subclasses herein.

In certain variations, provided are methods of making a compound of formula:

the method comprising reacting furfural with an alpha beta unsaturated acid, wherein R$^y$ is as defined above and in the classes and subclasses herein.

In certain embodiments, the methods include reacting furfural with an alpha beta unsaturated acid or ester having the formula:

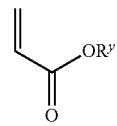

where R$^y$ is as defined above and in the classes and subclasses herein.

In certain variations, the methods include reacting furfural with an alpha beta unsaturated acid having the formula:

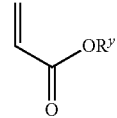

where R$^y$ is as defined above and in the classes and subclasses herein.

In certain embodiments, R$^y$ is —H. In certain embodiments, R$^y$ is C$_{1-20}$ aliphatic, or C$_{1-12}$ aliphatic, or C$_{1-8}$ aliphatic, or C$_{1-6}$ aliphatic, or C$_{1-4}$ aliphatic. In certain embodiments R$^y$ is selected from the group consisting of: methyl, ethyl, n-butyl, and 2ethylhexyl.

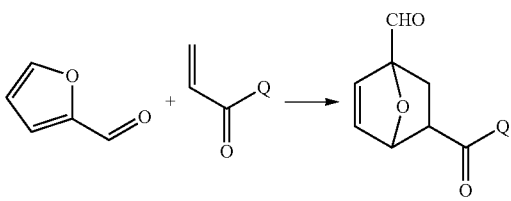

In certain embodiments, provided methods utilize a solid-supported alpha beta unsaturated acid. In certain embodiments, provided are methods of making a compound of Formula III:

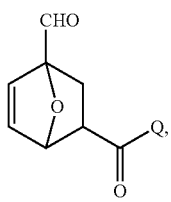

(III)

the method comprising reacting furfural with an alpha beta unsaturated acid having the formula:

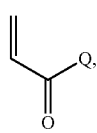

wherein Q is a solid support.

In certain embodiments, Q comprises an inorganic support. In certain embodiments, Q comprises an organic resin. In certain embodiments, the linkage to the solid support Q comprises an ester bond. In certain embodiments, the linkage to the solid support comprises an amide bond.

In certain embodiments, provided methods comprise hydrolyzing products of Formula III to release them from the solid support. In certain embodiments provided methods include contacting the compound of Formula III with an alcohol of formula ROR$^y$:

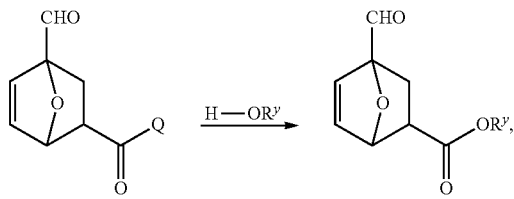

wherein each of O and R$^y$ is as defined above and in the classes and subclasses herein.

In certain embodiments, provided are methods of making a compound of formula:

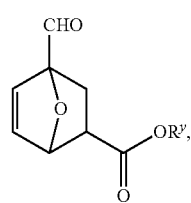

the method comprising treating a compound of formula

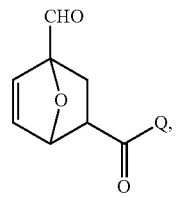

with a compound of formula H—OR$^y$, where each of Q and R$^y$ is as defined above and in the classes and subclasses herein. In certain embodiments, the reacting of furfural with the alpha beta unsaturated acid comprises heating a mixture of the furfural and the alpha beta unsaturated acid. In certain embodiments, the mixture is heated to a temperature between 50° C. and 300° C. In certain embodiments, the mixture is heated to a temperature between 50° C. and 150° C., between 100° C. and 200° C., between 120° C. and 180° C. or between 150° C. and 220° C. In certain embodiments, the heating of the mixture of the furfural and the alpha beta unsaturated acid comprises flowing the mixture through a heated plug flow reactor.

In certain embodiments, the reacting of furfural with the alpha beta unsaturated acid comprises contacting a mixture of the two substances with a catalyst. In certain embodiments, the catalyst is a Diels Alder catalyst. In certain embodiments, the catalyst is a Lewis acidic catalyst.

In certain aspects the provided methods utilize alpha beta unsaturated acids (or their esters, amides or thioesters) and acetals of furfural as starting materials to make aromatic diacids (or intermediates suitable for making such diacids). In certain aspects, provided are methods of making compounds including adducts of acrylic acid or its esters and furfural acetals, as well as aromatized and oxidized products of such adducts including aromatic dicarboxylic acids.

In certain embodiments, provided methods conform to the following scheme:

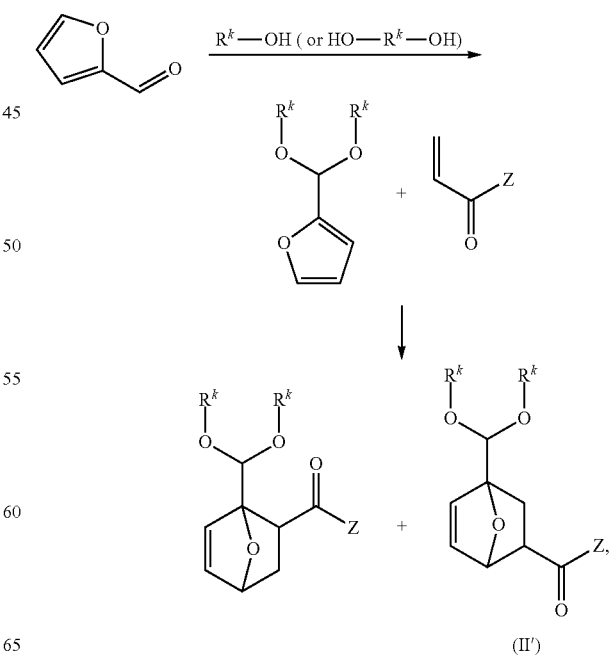

wherein each of $R^k$ and Z is as defined above and in the classes and subclasses herein.

In certain embodiments, Z is $OR^y$ and provided methods conform to the scheme:

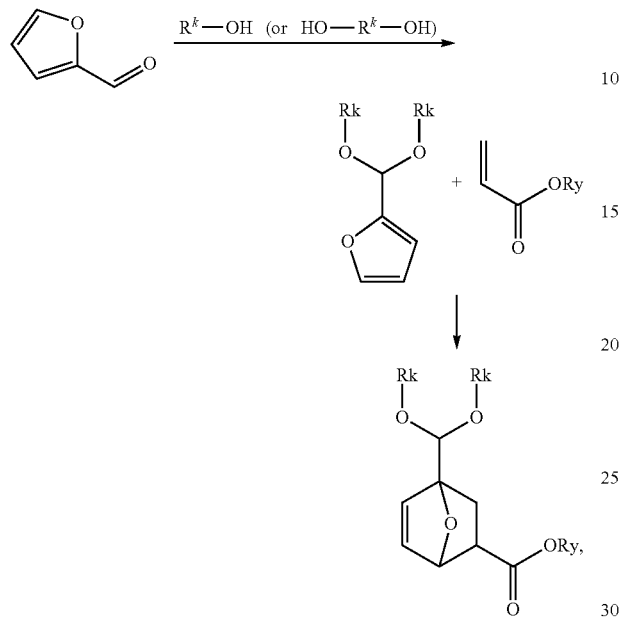

wherein each of $R^k$ and $R^y$ is as defined above and in the classes and subclasses herein.

In certain embodiments, provided are methods of making a compound of formula:

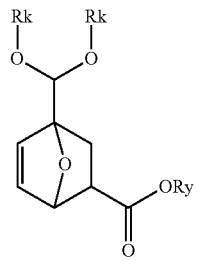

the method comprising
a) reacting furfural with an alcohol of formula $R^k$—OH (or HO—$R^k$—OH) under dehydrating conditions to provide an acetal compound of formula:

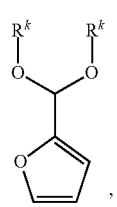

and
b) contacting the acetal with an alpha beta unsaturated acid or ester having formula:

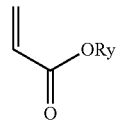

wherein:
$R^k$ is, independently at each occurrence, selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two $R^k$ may be taken with intervening atoms to form an optionally substituted 4- to 7-membered heterocyclic ring having 0-2 additional heteroatoms independently selected from the group consisting of nitrogen, oxygen, and sulfur, and $R^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In certain embodiments, $R^y$ is —H. In certain embodiments, $R^y$ is $C_{1-20}$ aliphatic, or $C_{1-12}$ aliphatic, or $C_{1-8}$ aliphatic, or $C_{1-6}$ aliphatic, or $C_{1-4}$ aliphatic. In certain embodiments $R^y$ is selected from the group consisting of: methyl, ethyl, n-butyl, and 2ethylhexyl.

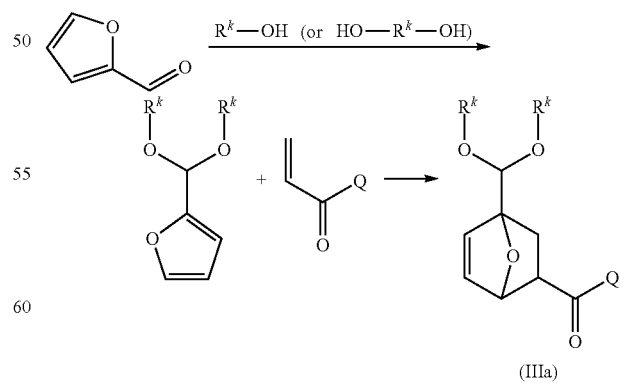

(IIIa)

In certain embodiments, provided methods utilize a solid-supported alpha beta unsaturated acid to react with a furfural acetal.

In certain embodiments, provided are methods of making a compound of Formula IIIa:

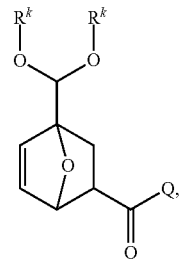
(IIIa)

the method comprising:
a) reacting furfural with an alcohol of formula $R^k$—OH (or HO—$R^k$—OH) under dehydrating conditions to provide an acetal compound of formula:

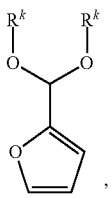

and
b) contacting the acetal with a alpha beta unsaturated acid having the formula:

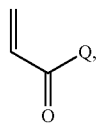

where Q is as defined above and in the classes and subclasses herein.

In certain embodiments, provided methods comprise hydrolyzing products of Formula IIIa to release them from the solid support. In certain embodiments provided methods include contacting the compound of Formula IIIa with an alcohol of formula HO—$R^y$:

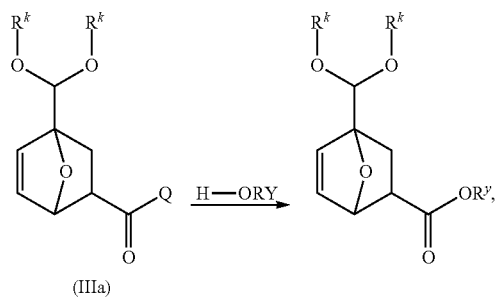
(IIIa)

wherein each of Q, $R^k$ and $R^Y$ is as defined above and in the classes and subclasses herein.

In certain embodiments, provided are methods of making a compound of formula:

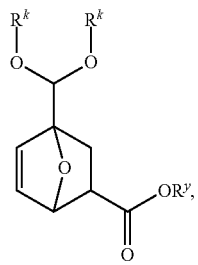

the method comprising treating a compound of Formula IIIa

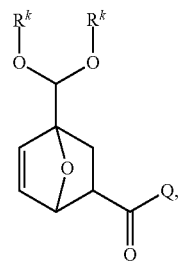
(IIIa)

with a compound of formula H-QR$^y$, wherein each of Q, $R^k$ and $R^y$ is as defined above and in the classes and subclasses herein.

In certain embodiments, the reacting of the acetal with the alpha beta unsaturated acid or ester comprises heating a mixture of the acetal and the alpha beta unsaturated acid or ester. In certain embodiments, the mixture is heated to a temperature between 50° C. and 300° C. In certain embodiments, the mixture is heated to a temperature between 50° C. and 150° C., between 100° C. and 200° C., between 120° C. and 180° C. or between 150° C. and 220° C. In certain embodiments, the heating of the mixture of the acetal and the alpha beta unsaturated acid or ester comprises flowing the mixture through a heated plug flow reactor.

In certain embodiments, the reacting of acetal with the alpha beta unsaturated acid or ester comprises contacting a mixture of the two substances with a catalyst. In certain embodiments, the catalyst is a Diels Alder catalyst. In certain embodiments, the catalyst is a Lewis acidic catalyst.

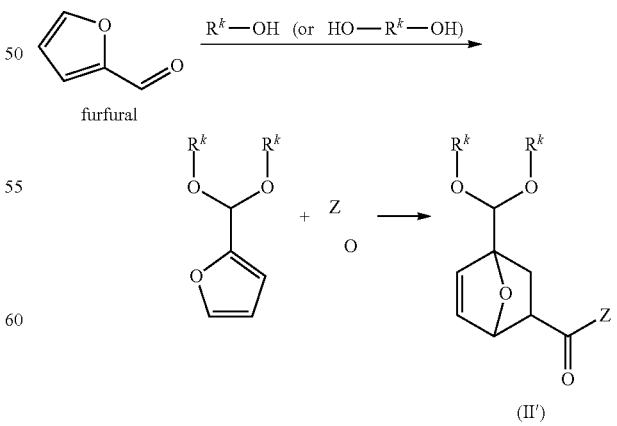
(II')

In some variations, provided are methods of making compounds of Formula II':

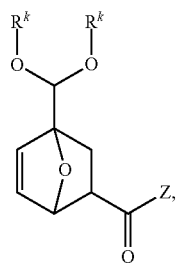
(II')

the method comprising:
a) reacting furfural with an alcohol of formula $R^k$—OH under dehydrating conditions to provide an acetal compound of formula:

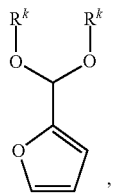, and
b) contacting the acetal with an alpha beta unsaturated acid, where Z and $R^k$ are as defined above and in the classes and subclasses herein.

In certain embodiments, provided are methods of making compounds of Formula II':

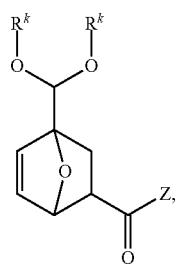
(II')

the method comprising:
a) reacting furfural with an alcohol of formula $R^k$—OH under dehydrating conditions to provide an acetal compound of formula:

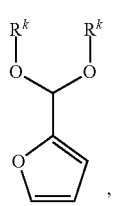, and
b) contacting the acetal with a compound of formula

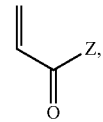

wherein Z and $R^k$ are as defined above and in the classes and subclasses herein.

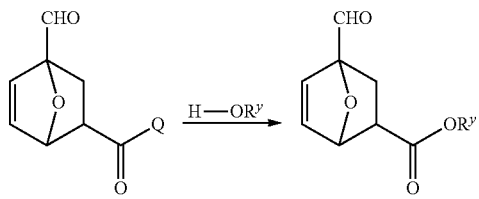

In certain embodiments, provided are methods of making a compound of formula:

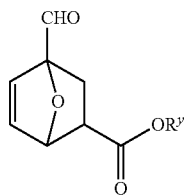

the method comprising treating a compound of formula

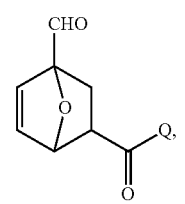

with a compound of formula H-QR$^y$, where each of Q and R$^y$ is as defined above and in the classes and subclasses herein.

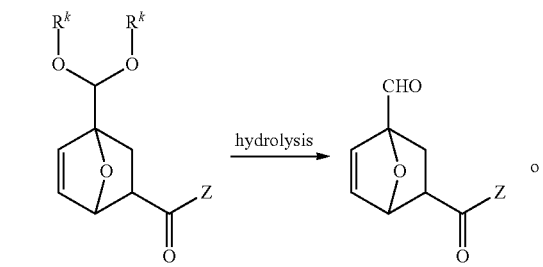

In certain embodiments, provided are methods of making a compound of Formula I':

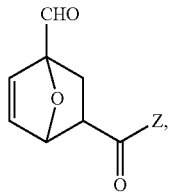
(I')

the method comprising hydrolyzing a compound of Formula II'

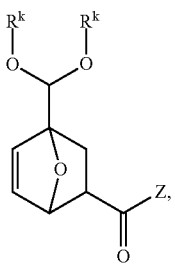
(II')

wherein each of Z and R$^k$ are as defined above and in the classes and subclasses herein.

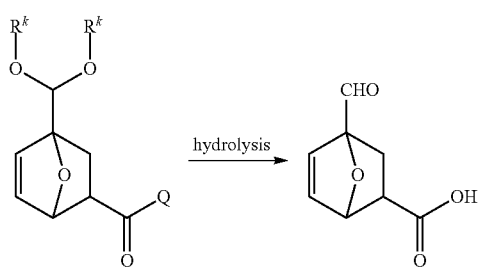

In certain embodiments, provided are methods of making a compound of formula:

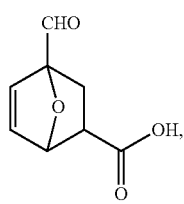 [SMILES: O=CC12C=CC(O1)C(C(=O)O)C2]

the method comprising hydrolyzing a compound of formula

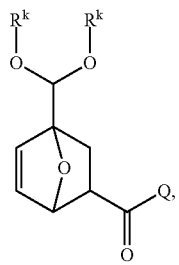

where each of Q and R$^k$ are as defined above and in the classes and subclasses herein.

The hydrolysis may be performed under any suitable conditions. For example, in some variations, the hydrolysis comprises heating the acetal in the presence of water. In certain embodiments, the hydrolysis comprises contacting the acetal with water in the presence of an acid. In certain embodiments, the hydrolysis comprises contacting the acetal with water in the presence of a base.

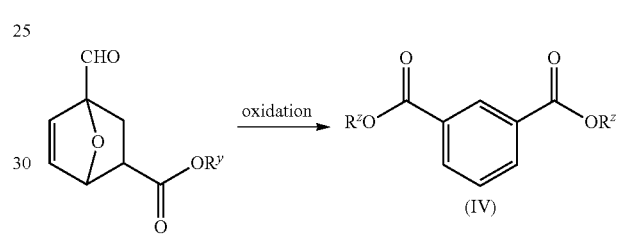
(IV)

In certain embodiments, provided are methods of making a compound of Formula IV:

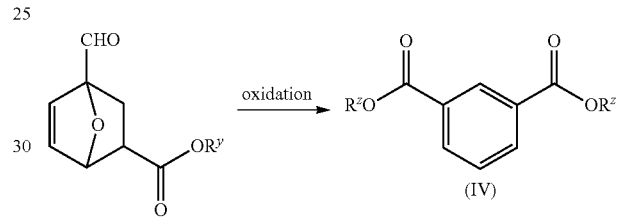
(IV)

wherein each R$^z$ is independently selected from the group consisting of: —H, IV', optionally substituted C$_{1-20}$ aliphatic, and optionally substituted aryl, the method comprising oxidizing a compound of formula:

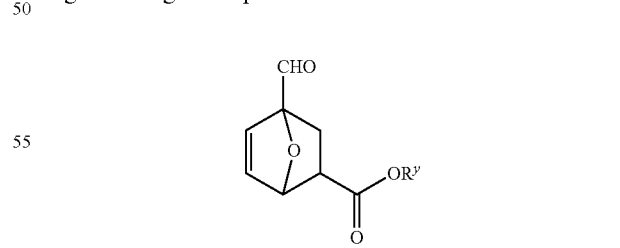

wherein R$^y$ is hydrogen, or an optionally substituted moiety selected the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In certain embodiments, provided are methods of making a compound of Formula IV:

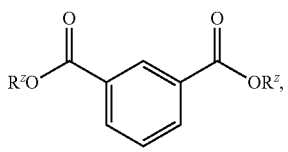
(IV)

the method comprising dehydrating and oxidizing a compound of formula:

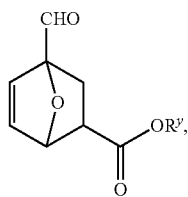

wherein:
R$^y$ is as defined above and in the classes and subclasses herein; and each
R$^Z$ is independently selected from the group consisting of: —H, R$^y$, optionally substituted C$_{1-20}$ aliphatic, and optionally substituted aryl.

In certain embodiments, the oxidizing of the compound of formula:

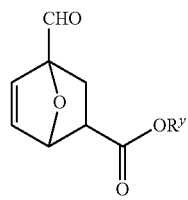

comprises heating the compound in the presence of air. In certain embodiments, the oxidizing step comprises heating the compound in the presence of air and a solid catalyst. In certain embodiments, the oxidizing step comprises heating the compound in the presence of air and an acidic compound. In certain embodiments, the oxidizing step is performed under conditions wherein water is continuously removed from the reaction mixture.

In certain embodiments, for the compound of formula:

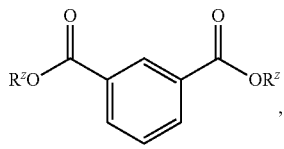

in the methods above, each R$^z$ is —H.

In certain embodiments, for the compound of formula:

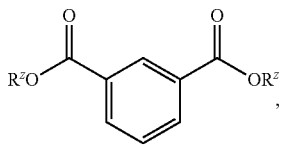

in the methods above, each R$^z$ is —CH3.

In certain embodiments of the above methods of making compounds of Formula IV, each R$^z$ is —H (e.g. compound of Formula IV is isophthalic acid). Where R$^z$ is —H, the hydrogen atom may derive from any proton source present during the dehydration or oxidation processes. Such proton sources may include for example, water, alcohols, organic acids, or mineral acids.

In certain embodiments of methods of making compounds of Formula IV, R$^z$ is optionally substituted C$_{1-20}$ aliphatic or optionally substituted aryl. Where R$^z$ is alkyl or aryl it may derive from an aliphatic or aromatic alcohol present in the dehydration or oxidation steps.

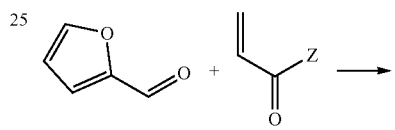

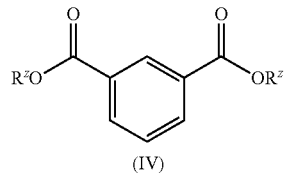
(IV)

In certain embodiments, provided are methods of making a compound of Formula IV: (IV),

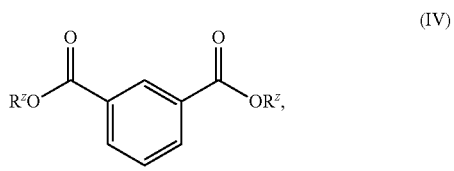
(IV)

wherein each R$^z$ is independently selected from the group consisting of: —H, R$^y$, optionally substituted C$_{1-20}$ aliphatic, and optionally substituted aryl, the method comprising contacting furfural with an alpha beta unsaturated carboxylic acid, (or an ester, amide or thioester thereof) and dehydrating and oxidizing the resulting product to produce the compound of Formula IV.

In certain variations, provided are methods of making a compound of Formula IV:

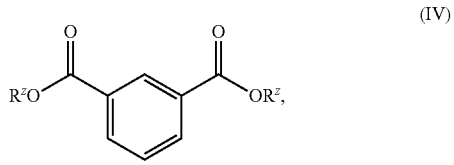
(IV)

the method comprising contacting furfural with an alpha beta unsaturated carboxylic acid (or a derivative thereof) and oxidizing the resulting product, where $R^z$ is as defined above and in the classes and subclasses herein.

In some variations, the alpha beta unsaturated carboxylic acid or derivative thereof is a compound of formula

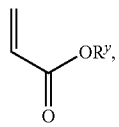

wherein $R^y$ is as defined above and in the classes and subclasses herein

In some variations, the alpha beta unsaturated carboxylic acid is acrylic acid.

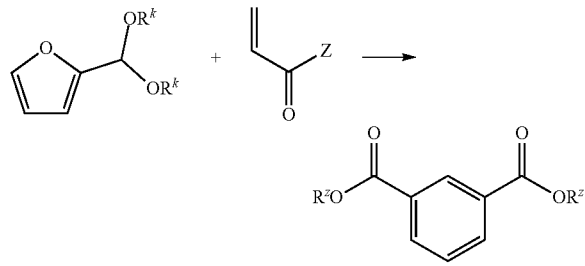

In certain embodiments, provided are methods of making a compound of Formula IV:

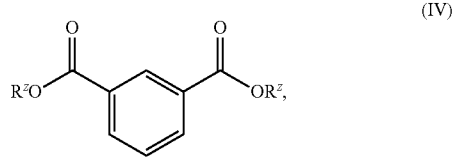

(IV)

wherein each $R^z$ is, independently at each occurrence, selected from the group consisting of: —H, $R^y$, optionally substituted $C_{1-20}$ aliphatic, and optionally substituted aryl, the method comprising contacting a compound of formula:

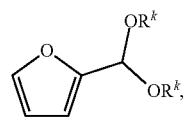

wherein each $R^k$ is, independently at each occurrence, selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two $R^k$ may be taken with intervening atoms to form an optionally substituted 4- to 7-membered heterocyclic ring having 0-2 additional heteroatoms independently selected from the group consisting of nitrogen, oxygen, and sulfur, with an alpha beta unsaturated acid (or an ester, amide, or thioester thereof) and oxidizing the resulting product to produce the compound of Formula IV.

In certain variations, provided are methods of making a compound of Formula IV:

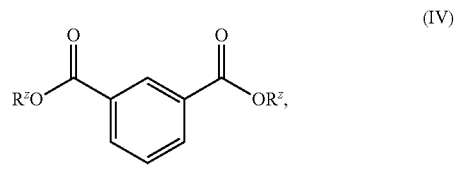

(IV)

the method comprising contacting a compound of formula:

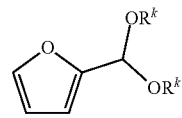

with an alpha beta unsaturated acid (or a derivative thereof) and oxidizing the resulting product, where each of $R^k$ and $R^z$ is as defined above and in the classes and subclasses herein.

In some variations, the alpha beta unsaturated carboxylic acid is a compound of formula

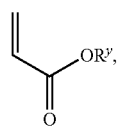

wherein $R^y$ is as defined above and in the classes and subclasses herein.

In some variations, the alpha beta unsaturated carboxylic acid is acrylic acid.

In certain embodiments of the above methods of making compounds of Formula IV, $R^z$ is —H (e.g. compound of Formula IV is isophthalic acid). Where $R^z$ is —H, the hydrogen atom may derive from any proton source present during the dehydration or oxidation processes. Such proton sources may include for example, water, alcohols, organic acids, or mineral acids.

In certain embodiments of methods of making compounds of Formula IV, $R^z$ is optionally substituted $C_{1-20}$ aliphatic or optionally substituted aryl. Where $R^z$ is alkyl or aryl it may derive from an aliphatic or aromatic alcohol present in the dehydration or oxidation steps.

Continuous Processes

In another aspect, provided are continuous processes for producing aromatic dicarboxylic acids and precursors thereof.

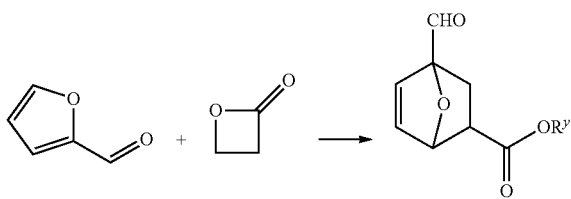

In some embodiments, provided is a continuous process for the production of compounds of formula:

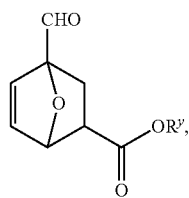

the continuous process comprising continuously feeding a reaction zone with furfural and BPL, and optionally an alcohol of formula HOR$^y$,
wherein R$^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

In some variations of the foregoing, when the alcohol of formula HOR$^y$ is absent, then R$^y$ is H with respect to the compound produced.

In certain embodiments, provided is a continuous process for the production of compounds of formula:

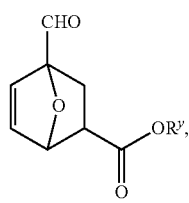

the continuous process comprising continuously feeding a reaction zone with furfural and BPL, where R$^y$ is as defined above and in the classes and subclasses herein.

In certain embodiments, the reaction zone fed with furfural and the BPL is heated. In certain embodiments, the reaction zone is heated to a temperature between 50° C. and 300° C. In certain embodiments, the reaction zone is heated to a temperature between 50° C. and 150° C., between 100° C. and 200° C., between 120° C. and 180° C., or between 150° C. and 220° C.

In certain embodiments, the reaction zone fed with furfural and the BPL contains a catalyst. In certain embodiments, the reaction zone contains a Lewis acidic catalyst. In certain embodiments, the reaction zone contains a heterogeneous Lewis acidic catalyst.

In certain embodiments, the process further includes withdrawing a product stream containing a compound of formula

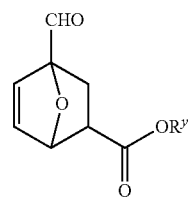

from the reaction zone.

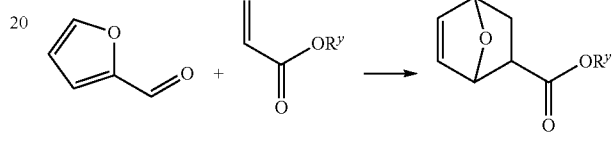

In certain embodiments, provided is a continuous process for the production of compounds of formula:

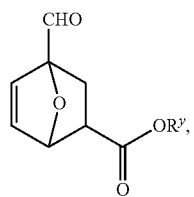

the continuous process comprising continuously feeding a reaction zone with furfural and an alpha beta unsaturated acid or ester, wherein R$^y$ is as defined above and in the classes and subclasses herein.

In some variations, the alpha beta unsaturated acid or ester is a compound of formula

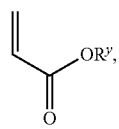

wherein R$^y$ is as defined above and in the classes and subclasses herein.

In certain embodiments, the reaction zone fed with furfural and the alpha beta unsaturated acid or ester is heated. In certain embodiments, the reaction zone is heated to a temperature between 50° C. and 300° C. In certain embodiments, the reaction zone is heated to a temperature between 50° C. and 150° C., between 100° C. and 200° C., between 120° C. and 180° C., or between 150° C. and 220° C.

In certain embodiments, the reaction zone fed with furfural and the alpha beta unsaturated acid or ester contains a catalyst. In certain embodiments, the reaction zone contains a Lewis acidic catalyst. In certain embodiments, the reaction zone contains a heterogeneous Lewis acidic catalyst.

In certain embodiments, the process further includes withdrawing a product stream containing a Diels Alder adduct of the furfural and an alpha beta unsaturated acid or ester from the reaction zone.

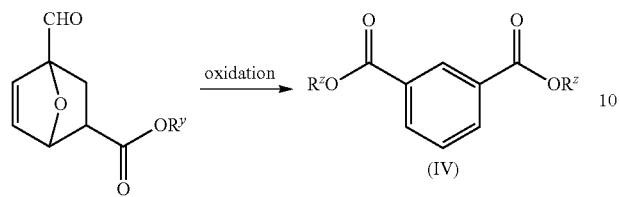

(IV)

In some embodiments, provided is a continuous process for making a compound of Formula IV:

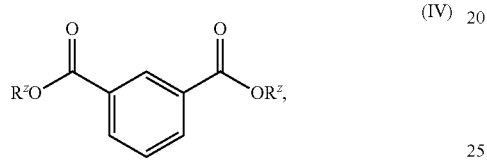

(IV)

wherein each $R^z$ is independently selected from the group consisting of: —H, $R^y$, optionally substituted $C_{1-20}$ aliphatic, and optionally substituted aryl, the process comprising continuously feeding to a reaction zone a compound of formula:

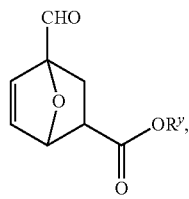

wherein $R^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5 to 10-membered heteroaryl having 1-4 heteroatoms independently selected from the group consisting of nitrogen, oxygen, and sulfur; 4 to 7-membered heterocyclic having 1-2 heteroatoms independently selected from the group consisting of nitrogen, oxygen, and sulfur; and an oxygen protecting group, where it is contacted with air, optionally in the presence of a catalyst to produce the compound of Formula IV.

In certain embodiments, the process includes providing a proton source in the reaction zone. In such embodiments, $R^z$ in compounds of Formula IV is —H (e.g. compound of Formula IV is isophthalic acid). Suitable proton sources include water, alcohols, organic acids, and mineral acids.

In certain embodiments, the process includes providing an alcohol ROH in the reaction zone. Suitable alcohols include aliphatic alcohols (e.g. $C_{1-20}$ alcohols) and aromatic alcohols. When an alcohol is present in the reaction zone, $R^z$ in the product may be —H, or $R^z$ may be a group corresponding to R in the provided alcohol or the product may comprise a mixture where $R^z$ groups are a mixture of —H and —R.

In certain embodiments, $R^z$ in compounds of Formula IV may represent a mixture including groups corresponding to any combination of $R^y$ (e.g., from the starting material), —H, and R (e.g., from the alcohol ROH if it is present in the reaction zone).

In certain embodiments, provided is a continuous process for making a compound of Formula IV:

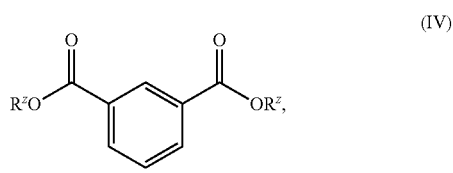

(IV)

the process comprising continuously feeding to a reaction zone a compound of formula:

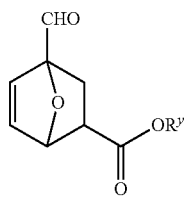

where it is contacted with air, optionally in the presence of a catalyst.

In certain embodiments, the reaction zone is heated. In certain embodiments, the reaction zone is heated to a temperature between 100° C. and 500° C. In certain embodiments, the reaction zone is heated to a temperature between 100° C. and 200° C., between 120° C. and 180° C., between 150° C. and 220° C., between 200° C. and 300° C., or between 300° C. and 450° C.

In certain embodiments, the reaction zone comprises an acid catalyst. In certain embodiments, the reaction zone contains sulfuric acid. In certain embodiments, the reaction zone comprises a heterogeneous catalyst. In certain embodiments, the reaction zone comprises a solid acid catalyst.

In certain embodiments, the process further includes continuously withdrawing a product stream containing isophthalic acid or an ester thereof from the reaction zone. In certain embodiments, the process further includes a step of purifying the isophthalic acid (or esters thereof) withdrawn from the reaction zone. In certain embodiments, the purification includes distillation, crystallization, or a combination of both of these.

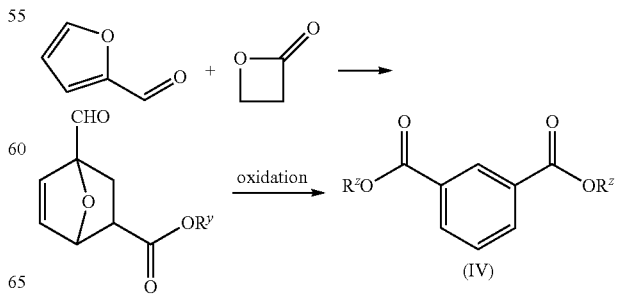

(IV)

In some embodiments, provided is a continuous process for making a compound of Formula IV:

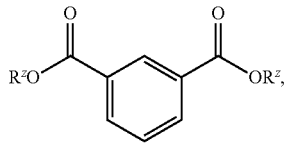
(IV)

wherein $R^z$ is independently selected from the group consisting of: —H, $R^y$, optionally substituted $C_{1-20}$ aliphatic, and optionally substituted aryl, the process comprising continuously feeding a first reaction zone with furfural and BPL, and optionally an alcohol of formula $HOR^y$, wherein $R^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group, to produce a compound of formula:

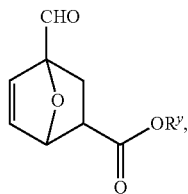

which is fed to a second reaction zone where it is contacted with air, optionally in the presence of a catalyst to produce the compound of Formula IV.

In certain embodiments, the process includes providing a proton source in the second reaction zone. In such embodiments, $R^z$ in compounds of Formula IV is —H (e.g. compound of Formula IV is isophthalic acid). Suitable proton sources include water, alcohols, organic acids, and mineral acids.

In certain embodiments, the process includes providing an alcohol ROH in the second reaction zone. Suitable alcohols include aliphatic alcohols (e.g. $C_{1-20}$ alcohols) and aromatic alcohols. When an alcohol is present in the second reaction zone, $R^z$ in the product may be —H, or $R^z$ may be a group corresponding to R in the provided alcohol or the product may comprise a mixture where $R^z$ groups are a mixture of —H and —R.

In certain embodiments, $R^z$ in compounds of Formula IV may represent a mixture including groups corresponding to any combination of $R^y$ (e.g., from the starting material), —H, and R (e.g., from the alcohol ROH if it is present in the second reaction zone).

In some variations of the foregoing, when the alcohol of formula $HOR^y$ is absent, then $R^y$ is H with respect to the compound of formula

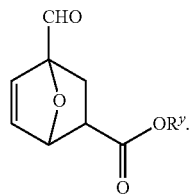

In certain embodiments, provided is a continuous process for making a compound of Formula:

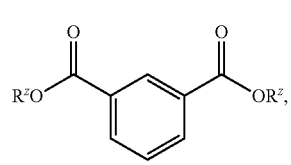
(IV)

the process comprising continuously feeding a first reaction zone with furfural and BPL, to produce a compound of formula:

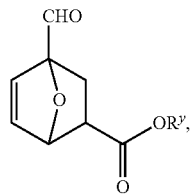

which is fed to a second reaction zone where it is contacted with air, optionally in the presence of a catalyst.

In certain embodiments, the first reaction zone is heated. In certain embodiments, the first reaction zone is heated to a temperature between 50° C. and 300° C. In certain embodiments, the reaction zone is heated to a temperature between 50° C. and 150° C., between 100° C. and 200° C., between 120° C. and 180° C., or between 150° C. and 220° C.

In certain embodiments, the first reaction zone contains a catalyst. In certain embodiments, the first reaction zone contains a Lewis acidic catalyst. In certain embodiments, the first reaction zone contains a heterogeneous Lewis acidic catalyst.

In certain embodiments, the second reaction zone is heated. In certain embodiments, the second reaction zone is heated to a temperature between 100° C. and 500° C. In certain embodiments, the reaction zone is heated to a temperature between 100° C. and 200° C., between 120° C. and 180° C., between 150° C. and 220° C., between 200° C. and 300° C., or between 300° C. and 450° C.

In certain embodiments, the second reaction zone comprises an acid catalyst. In certain embodiments, the second reaction zone contains sulfuric acid. In certain embodiments, the second reaction zone comprises a heterogeneous catalyst. In certain embodiments, the second reaction zone comprises a solid acid catalyst.

In certain embodiments, the process further includes continuously withdrawing a product stream containing isophthalic acid or an ester thereof from the second reaction zone. In certain embodiments, the process further includes purifying the isophthalic acid (or esters thereof) withdrawn from the second reaction zone. In certain embodiments, the purification includes distillation, crystallization, or a combination of both of these.

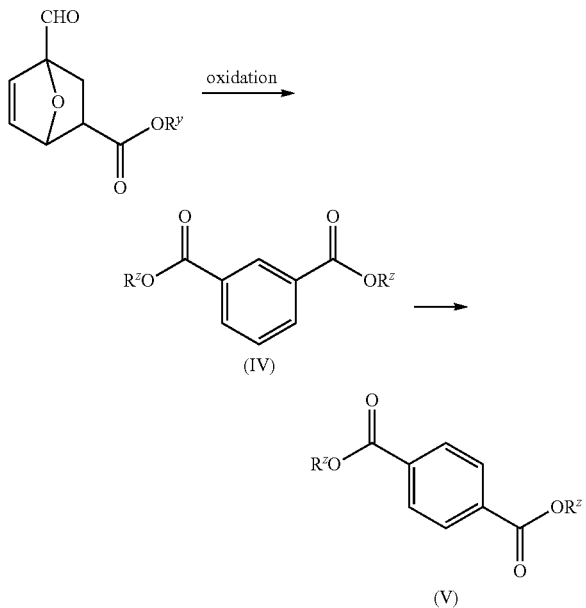

certain embodiments, provided is a continuous process for making a compound of Formula V:

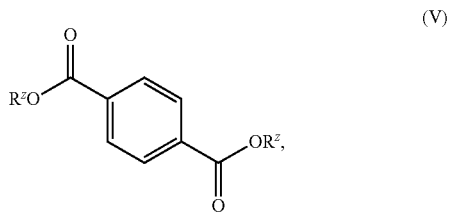

wherein $R^z$ is independently selected from the group consisting of: —H, $R^y$, optionally substituted $C_{1-20}$ aliphatic, and optionally substituted aryl, the process comprising continuously feeding to an oxidizing reaction zone a compound of formula:

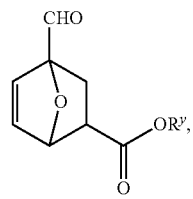

wherein it is contacted with air, optionally in the presence of a catalyst to form a compound of Formula IV:

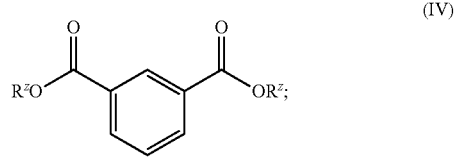

and then, either within the same reaction zone or in a subsequent rearrangement reaction zone, converted to a compound of Formula (V).

In certain embodiments, the process includes providing a proton source in the oxidizing reaction zone. In such embodiments, $R^z$ in compounds of Formula V is —H (e.g. compound of Formula V is terephthalic acid). Suitable proton sources include water, alcohols, organic acids, and mineral acids.

In certain embodiments, the process includes providing an alcohol ROH in the oxidizing reaction zone. Suitable alcohols include aliphatic alcohols (e.g. $C_{1-20}$ alcohols) and aromatic alcohols. When an alcohol is present in the second reaction zone, $R^z$ in the product may be —H, or $R^z$ may be a group corresponding to R in the provided alcohol or the product may comprise a mixture where $R^z$ groups are a mixture of —H and —R.

In certain embodiments, $R^z$ in compounds of V may represent a mixture including groups corresponding to any combination of $R^y$ (e.g., from the starting material), —H, and R (e.g., from the alcohol ROH if it is present in the oxidizing reaction zone).

In certain embodiments, provided is a continuous process for making a compound of Formula V:

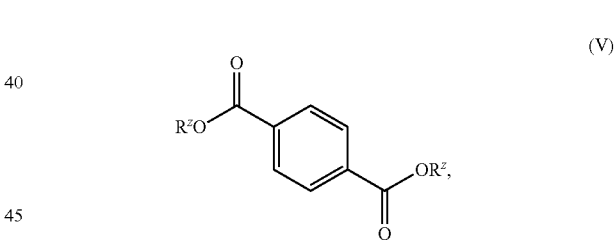

the process comprising continuously feeding a first reaction zone with furfural or a derivative thereof and BPL to provide a product of formula:

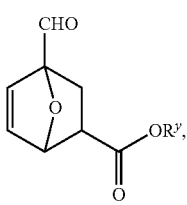

which is fed to a second reaction zone where it is contacted with air, optionally in the presence of a catalyst to form a compound of formula;

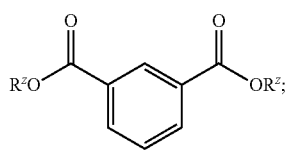

and then, either within the same reaction zone or in a subsequent rearrangement reaction zone, converted to a compound of Formula V, wherein each of $R^z$, and $R^y$ are as defined above and in the classes and subclasses herein.

In certain embodiments of this process, the oxidation reaction zone and the rearrangement reaction zone are contiguous and the process stream flows from a reactor inlet through an oxidation zone and into a rearrangement zone. In certain embodiments, there is a temperature gradient whereby the rearrangement reaction zone is maintained at a higher temperature than the oxidation reaction zone.

In certain embodiments, the oxidation reaction zone is heated. In certain embodiments, the oxidation reaction zone is heated to a temperature between 100° C. and 300° C. In certain embodiments, the reaction zone is heated to a temperature between 100° C. and 200° C., between 120° C. and 180° C., between 150° C. and 220° C., or between 200° C. and 250° C.

In certain embodiments, the rearrangement reaction zone is heated. In certain embodiments, the reaction zone is heated to a temperature between 300° C. and 500° C. In certain embodiments, the reaction zone is heated to a temperature between 300° C. and 400° C., between 350° C. and 450° C., between 400° C. and 500° C., between 400° C. and 450° C., or between 450° C. and 500° C.

In certain embodiments, the oxidation reaction zone comprises a catalyst. In certain embodiments, the oxidation reaction zone comprises an acid catalyst. In certain embodiments, the oxidation reaction zone contains sulfuric acid. In certain embodiments, the oxidation reaction zone comprises a heterogeneous catalyst. In certain embodiments, the oxidation reaction zone comprises a solid acid catalyst.

In certain embodiments, the rearrangement reaction zone comprises a catalyst. In certain embodiments, the rearrangement reaction zone comprises a transition metal catalyst. In certain embodiments, the rearrangement reaction zone contains a cadmium-based catalyst. In certain embodiments, the rearrangement reaction zone comprises a heterogeneous catalyst. In certain embodiments, the rearrangement reaction zone comprises a heterogeneous transition metal catalyst. In certain embodiments, the rearrangement reaction zone comprises a solid cadmium-containing catalyst.

In certain embodiments, the process includes providing a proton source in the one or more of the oxidation reaction zone and the rearrangement reaction zone. In such embodiments, $R^z$ in compounds of Formula V is —H (e.g. compound of Formula V is terephthalic acid). Suitable proton sources include water, alcohols, organic acids, and mineral acids.

In certain embodiments, the process includes providing an alcohol ROH in the one or more of the oxidation reaction zone and the rearrangement reaction zone. Suitable alcohols include aliphatic alcohols (e.g. $C_{1-20}$ alcohols) and aromatic alcohols. When an alcohol is present in the second reaction zone, $R^z$ in the product may be —H, or $R^z$ may be a group corresponding to R in the provided alcohol or the product may comprise a mixture where $R^z$ groups are a mixture of —H and —R.

In certain embodiments, $R^z$ in compounds of Formula V may represent a mixture including groups corresponding to any combination of $R^y$ (e.g., from the starting material), —H, and R (e.g., from the alcohol ROH if it is present one or more reaction zones).

In certain embodiments, the process further includes continuously withdrawing a product stream containing terephthalic acid or an ester thereof from the rearrangement reaction zone. In certain embodiments, the process includes withdrawing a product stream containing terephthalic acid or an ester thereof which also contains one or more coproducts selected from benzene, benzoic acid (or esters thereof), phthalic acid (or esters thereof), and isophthalic acid (or esters thereof). In certain embodiments the process further includes a step of separating terephthalic acid (or esters thereof) from one or more of these co-products. In certain embodiments the separating process includes one or more of distillation, and crystallization.

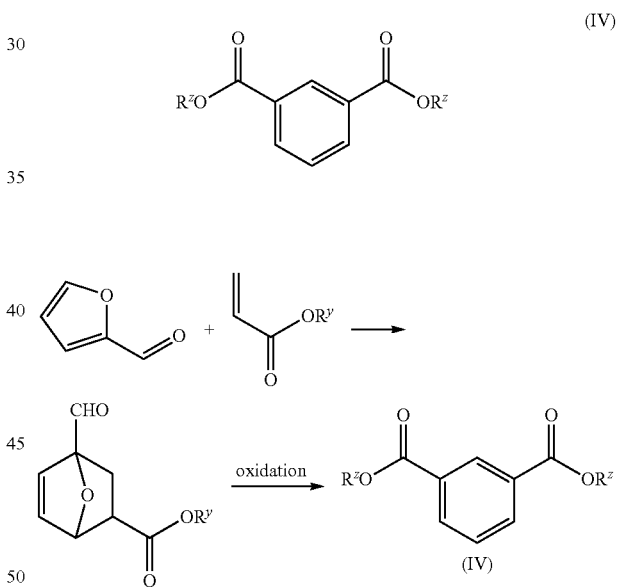

In certain embodiments, provided is a continuous process for the production of compounds of Formula IV:

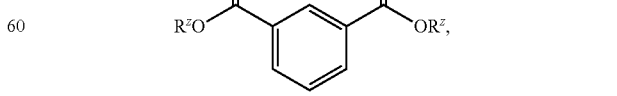

the continuous process comprising continuously feeding a Diels Alder reaction zone with furfural and an alpha beta unsaturated acid or ester, to provide a compound of formula:

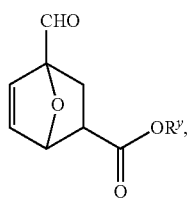

and
further comprising feeding this compound to an oxidation reaction zone, where it is oxidized to a compound of Formula IV,
wherein each of $R^z$ and $R^y$ are as defined above and in the classes and subclasses herein.

In some variations, the alpha beta unsaturated acid or ester is

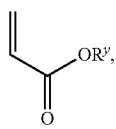

wherein $R^y$ is as defined above and in the classes and subclasses herein.

In certain embodiments, the Diels Alder reaction zone is heated. In certain embodiments, the Diels Alder reaction zone is heated to a temperature between 50° C. and 300° C. In certain embodiments, the Diels Alder reaction zone is heated to a temperature between 50° C. and 150° C., between 100° C. and 200° C., between 120° C. and 180° C., or between 150° C. and 220° C.

In certain embodiments, the Diels Alder reaction zone contains a catalyst. In certain embodiments, the Diels Alder reaction zone contains a Lewis acidic catalyst. In certain embodiments, the reaction zone contains a heterogeneous Lewis acidic catalyst.

In certain embodiments, the process further includes purifying a product stream obtained from the Diels Alder reaction zone prior to inputting it to the oxidation reaction zone. In certain embodiments, the purifying step comprises distilling away unreacted furfural or alpha beta unsaturated acids or esters. In certain embodiments, these materials are returned to the inlet of the Diels Alder reaction zone for further conversion. In certain embodiments, the purifying comprises crystallizing Diels Alder adducts from the product stream and separating the crystalline material from dissolved materials. In certain embodiments, the dissolved fraction is returned to the inlet of the Diels Alder reaction zone.

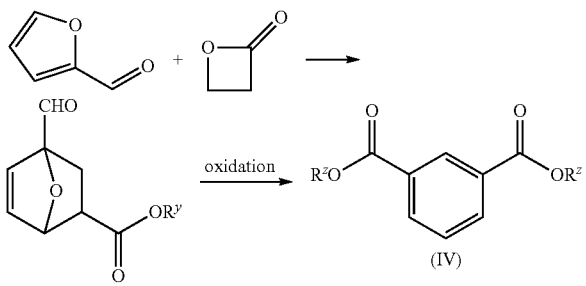

In some embodiments, provided is a continuous process for the production of compounds of Formula IV:

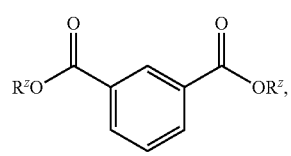

the continuous process comprising continuously feeding a first reaction zone with furfural and BPL, and optionally an alcohol of formula $HOR^y$, to provide a compound of formula:

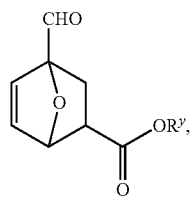

and
wherein $R^y$ is hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group; and feeding this compound to an oxidation reaction zone, where it is oxidized to a compound of Formula IV.

In certain embodiments, the process includes providing a proton source in the oxidizing reaction zone. In such embodiments, $R^z$ in compounds of Formula IV is —H (e.g. compound of Formula IV is isophthalic acid). Suitable proton sources include water, alcohols, organic acids, and mineral acids.

In certain embodiments, the process includes providing an alcohol ROH in the oxidizing reaction zone. Suitable alcohols include aliphatic alcohols (e.g. $C_{1-20}$ alcohols) and aromatic alcohols. When an alcohol is present in the second reaction zone, $R^z$ in the product may be —H, or $R^z$ may be a group corresponding to R in the provided alcohol or the product may comprise a mixture where $R^z$ groups are a mixture of —H and —R.

In certain embodiments, $R^z$ in compounds of Formula IV may represent a mixture including groups corresponding to any combination of $R^y$ (e.g., from the starting material), —H, and R (e.g., from the alcohol ROH if it is present in the oxidizing reaction zone).

In some variations of the foregoing, when the alcohol of formula $HOR^y$ is absent, then $R^y$ is H with respect to the compound of formula

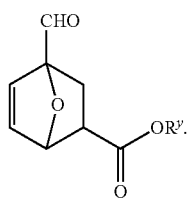

In certain embodiments, provided is a continuous process for the production of compounds of formula:

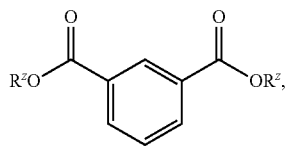

the continuous process comprising continuously feeding a first reaction zone with furfural and BPL, to provide a compound of formula:

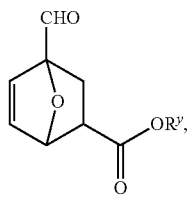

and
further comprising feeding this compound to an oxidation reaction zone, where it is oxidized to a compound of formula

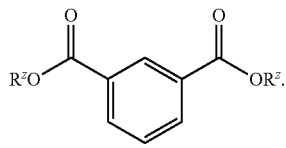

In certain embodiments, the first reaction zone is heated. In certain embodiments, the first reaction zone is heated to a temperature between 50° C. and 300° C. In certain embodiments, the first reaction zone is heated to a temperature between 50° C. and 150° C., between 100° C. and 200° C., between 120° C. and 180° C., or between 150° C. and 220° C.

In certain embodiments, the first reaction zone contains a catalyst. In certain embodiments, the first reaction zone contains a Lewis acidic catalyst. In certain embodiments, the first reaction zone contains a heterogeneous Lewis acidic catalyst.

In certain embodiments, the process further includes purifying a product stream obtained from the first zone prior to inputting it to the oxidation reaction zone. In certain embodiments the purifying step comprises distilling away unreacted furfural or alpha beta unsaturated acids or esters. In certain embodiments, these materials are returned to the inlet of the first reaction zone for further conversion. In certain embodiments, the step of purifying comprises crystallizing product from the product stream and separating the crystalline material from dissolved materials. In certain embodiments, the dissolved fraction is returned to the inlet of the first reaction zone.

In certain embodiments, the oxidation reaction zone is heated. In certain embodiments, the oxidation reaction zone is heated to a temperature between 100° C. and 500° C. In certain embodiments, the oxidation reaction zone is heated to a temperature between 100° C. and 200° C., between 120° C. and 180° C., between 150° C. and 220° C., between 200° C. and 300° C., or between 300° C. and 450° C.

In certain embodiments, the oxidation reaction zone comprises an acid catalyst. In certain embodiments, the oxidation reaction zone contains sulfuric acid. In certain embodiments, the oxidation reaction zone comprises a heterogeneous catalyst. In certain embodiments, the oxidation reaction zone comprises a solid acid catalyst.

In certain embodiments, the process further includes continuously withdrawing a product stream containing isophthalic acid or an ester thereof from the oxidation reaction zone. In certain embodiments, the process further includes a step of purifying the isophthalic acid (or esters thereof) withdrawn from the oxidation reaction zone. In certain embodiments, the purification includes distillation, crystallization, or a combination of both of these.

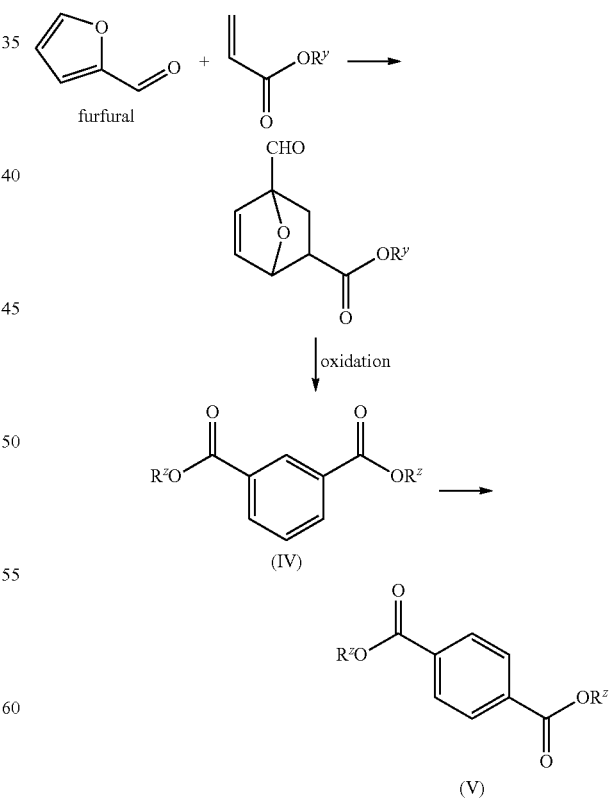

In some embodiments, provided is a continuous process for making a compound of Formula V:

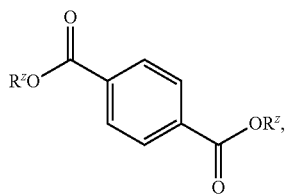

(V)

wherein $R^z$ is independently selected from the group consisting of: —H, $R^y$, optionally substituted $C_{1-20}$ aliphatic, and optionally substituted aryl, the continuous process comprising continuously feeding a Diels Alder reaction zone with furfural and an alpha beta unsaturated acid or ester, to provide a compound of formula:

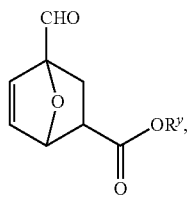

wherein $R^y$ is hydrogen, or an optionally substituted moiety selected the group consisting of: acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group; feeding the compound to an oxidation reaction zone where it is contacted with air, optionally in the presence of a catalyst, to form a compound of Formula IV:

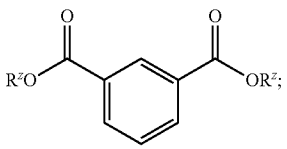

(IV)

and
feeding the compound of Formula IV to a rearrangement reaction zone, where it is converted to a compound of Formula V.

In certain embodiments, the process includes providing a proton source in the oxidizing reaction zone. In such embodiments, $R^z$ in compounds of Formula V is —H (e.g. compound of Formula V is terephthalic acid). Suitable proton sources include water, alcohols, organic acids, and mineral acids.

In certain embodiments, the process includes providing an alcohol ROH in the oxidizing reaction zone. Suitable alcohols include aliphatic alcohols (e.g. $C_{1-20}$ alcohols) and aromatic alcohols. When an alcohol is present in the second reaction zone, $R^z$ in the product may be —H, or $R^z$ may be a group corresponding to R in the provided alcohol or the product may comprise a mixture where $R^z$ groups are a mixture of —H and —R.

In certain embodiments, $R^z$ in compounds of Formula V may represent a mixture including groups corresponding to any combination of $R^y$ (e.g., from the starting material), —H, and R (e.g., from the alcohol ROH if it is present in the oxidizing reaction zone).

In certain embodiments, provided is a continuous process for making a compound of formula:

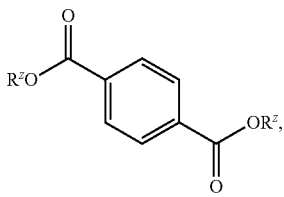

the continuous process comprising continuously feeding a Diels Alder reaction zone with furfural and an alpha beta unsaturated acid or ester, to provide a compound of formula:

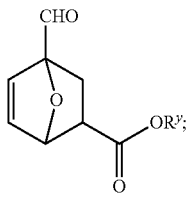

which is then fed to an oxidation reaction zone where it is contacted with air, optionally in the presence of a catalyst, to form a compound of formula:

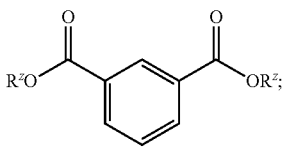

which is then fed to a rearrangement reaction zone, where it is converted to a compound of formula:

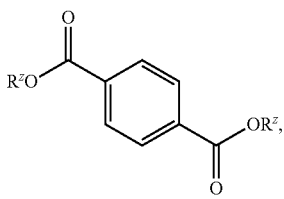

wherein each of $R^z$, and $R^y$ are as defined above and in the classes and subclasses herein.

In certain embodiments of the processes described herein, the Die Is Alder reaction zone is heated. In certain embodiments, the Diels Alder reaction zone is heated to a temperature between 50° C. and 300° C. In certain embodiments, the Diels Alder reaction zone is heated to a temperature between 50° C. and 150° C., between 100° C. and 200° C., between 120° C. and 180° C., or between 150° C. and 220° C.

In certain embodiments, the Diels Alder reaction zone contains a catalyst. In certain embodiments, the Diels Alder reaction zone contains a Lewis acidic catalyst. In certain embodiments, the reaction zone contains a heterogeneous Lewis acidic catalyst.

In certain embodiments, the processes described herein further include purifying a product stream obtained from the Diels Alder reaction zone prior to inputting it to the oxidation reaction zone. In certain embodiments the purifying step comprises distilling away unreacted furfural or alpha beta unsaturated acids or esters. In certain embodiments, these materials are returned to the inlet of the Diels Alder reaction zone for further conversion. In certain embodiments, the step of purifying comprises crystallizing Diels Alder adducts from the product stream and separating the crystalline material from dissolved materials. In certain embodiments, the dissolved fraction is returned to the inlet of the Diels Alder reaction zone.

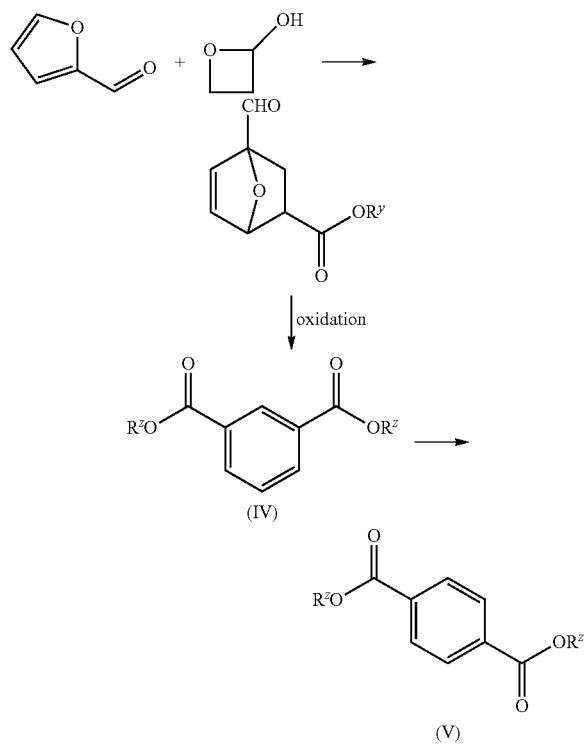

In some embodiments, provided is a continuous process for making a compound of Formula V:

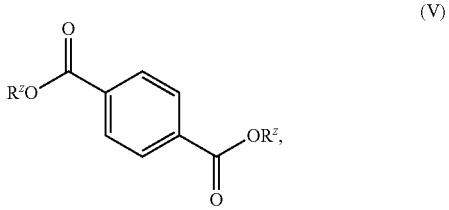

wherein $R^z$ is independently selected from the group consisting of: —H, $R^y$, optionally substituted $C_{1-20}$ aliphatic, and optionally substituted aryl, the continuous process comprising continuously feeding a first reaction zone with furfural and BPL, and optionally an alcohol of formula $HOR^y$, to provide a compound of formula:

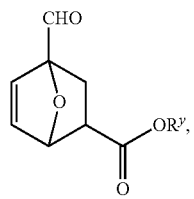

and wherein $R^y$ is hydrogen, or an optionally substituted moiety selected the group consisting of: acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group, to provide a compound of formula:

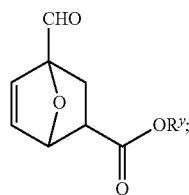

feeding the compound to an oxidizing reaction zone where it is contacted with air, optionally in the presence of a catalyst, to form a compound of Formula IV:

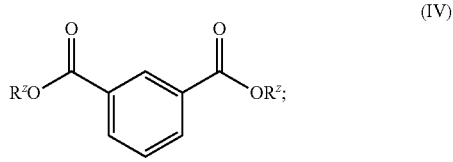

which is then fed to a rearrangement reaction zone, where it is converted to a compound of Formula V.

In certain embodiments, the process includes providing a proton source in the one or more of the oxidation reaction zone and the rearrangement reaction zone. In such embodiments, $R^z$ in compounds of Formula V is —H (e.g. compound of Formula V is terephthalic acid). Suitable proton sources include water, alcohols, organic acids, and mineral acids.

In certain embodiments, the process includes providing an alcohol ROH in the one or more of the oxidation reaction zone and the rearrangement reaction zone. Suitable alcohols include aliphatic alcohols (e.g. $C_{1-20}$ alcohols) and aromatic alcohols. When an alcohol is present in the second reaction zone, $R^z$ in the product may be —H, or $R^z$ may be a group corresponding to R in the provided alcohol or the product may comprise a mixture where $R^z$ groups are a mixture of —H and —R.

In certain embodiments, $R^z$ in compounds of Formula V may represent a mixture including groups corresponding to any combination of $R^y$ (e.g., from the starting material), —H, and R (e.g., from the alcohol ROH if it is present one or more reaction zones).

In some variations of the foregoing, when the alcohol of formula HOR$^y$ is absent, then R$^y$ is H with respect to the compound of formula

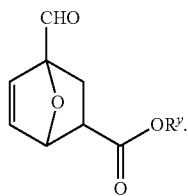

In certain embodiments, provided is a continuous process for making a compound of formula:

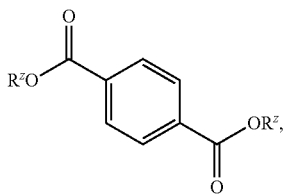

the continuous process comprising continuously feeding a first reaction zone with furfural and BPL, to provide a compound of formula:

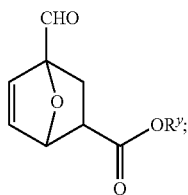

which is then fed to an oxidizing reaction zone where it is contacted with air, optionally in the presence of a catalyst, to form a compound of formula:

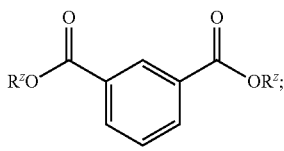

which is then fed to a rearrangement reaction zone, where it is converted to a compound of formula:

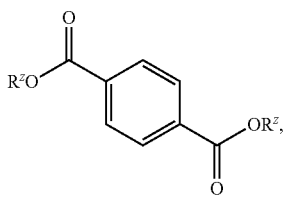

where each of R$^z$ and R$^y$ are independently as defined above and in the classes and subclasses herein.

In certain embodiments of the processes described herein, the first reaction zone is heated. In certain embodiments, the first reaction zone is heated to a temperature between 50° C. and 300° C. In certain embodiments, the first reaction zone is heated to a temperature between 50° C. and 150° C., between 100° C. and 200° C., between 120° C. and 180° C., or between 150° C. and 220° C.

In certain embodiments of the processes described herein, the first reaction zone contains a catalyst. In certain embodiments, the first reaction zone contains a Lewis acidic catalyst. In certain embodiments, the first reaction zone contains a heterogeneous Lewis acidic catalyst.

In certain embodiments, the processes described herein further include purifying a product stream obtained from the first reaction zone prior to inputting it to the oxidation reaction zone. In certain embodiments the purifying step comprises distilling away unreacted furfural, BPL, or alpha beta unsaturated acids or esters. In certain embodiments, these materials are returned to the inlet of the first reaction zone for further conversion. In certain embodiments, the step of purifying comprises crystallizing products from the product stream and separating the crystalline material from dissolved materials. In certain embodiments, the material from the dissolved fraction is returned to the inlet of the first reaction zone.

In certain embodiments of the processes described herein, the oxidation reaction zone is heated. In certain embodiments, the oxidation reaction zone is heated to a temperature between 100° C. and 300° C. In certain embodiments, the reaction zone is heated to a temperature between 100° C. and 200° C., between 120° C. and 180° C., between 150° C. and 220° C., or between 200° C. and 250° C.

In certain embodiments of the processes described herein, the oxidation reaction zone comprises a catalyst. In certain embodiments, the oxidation reaction zone comprises an acid catalyst. In certain embodiments, the oxidation reaction zone contains sulfuric acid. In certain embodiments, the oxidation reaction zone comprises a heterogeneous catalyst. In certain embodiments, the oxidation reaction zone comprises a solid acid catalyst.

In certain embodiments of the processes described herein, the rearrangement reaction zone is heated. In certain embodiments, the reaction zone is heated to a temperature between 300° C. and 500° C. In certain embodiments, the reaction zone is heated to a temperature between 300° C. and 400° C., between 350° C. and 450° C., between 400° C. and 500° C., between 400° C. and 450° C., or between 450° C. and 500° C.

In certain embodiments, the rearrangement reaction zone comprises a catalyst. In certain embodiments, the rearrangement reaction zone comprises a transition metal catalyst. In certain embodiments, the rearrangement reaction zone contains a cadmium based catalyst. In certain embodiments, the rearrangement reaction zone comprises a heterogeneous catalyst. In certain embodiments, the rearrangement reaction zone comprises a heterogeneous transition metal catalyst. In certain embodiments, the rearrangement reaction zone comprises a solid cadmium-containing catalyst.

In certain embodiments of the processes described herein, the oxidation reaction zone and the rearrangement reaction zone are contiguous and the process stream flows from a reactor inlet through an oxidation zone and into a rearrangement zone. In certain embodiments, there is a temperature gradient whereby the rearrangement reaction zone is maintained at a higher temperature than the oxidation reaction zone.

In certain embodiments of the processes described herein, the product of the oxidation reaction zone is converted to a salt prior to being fed to the rearrangement reaction zone. In certain embodiments of this process, the product of the oxidation reaction zone is converted to its alkali metal salt prior to being fed to the rearrangement reaction zone. In certain embodiments of this process, the product of the oxidation reaction zone is converted to its potassium salt prior to being fed to the rearrangement reaction zone. In some variations of this process, the product of the oxidation reaction zone is converted to its alkali metal salt prior to being fed to the rearrangement reaction zone. In other variations of this process, the stream withdrawn from the rearrangement reaction zone is subsequently treated with an acid to convert the alkali metal salt of the terephthalic acid back to its acid form, or optionally with inclusion of an appropriate alcohol or similar reagent to a terephthalate ester. In certain embodiments of this process, the stream withdrawn from the rearrangement reaction zone is subsequently treated with an acid to convert the alkali metal salt of the terephthalic acid back to its acid form, or optionally with inclusion of an appropriate alcohol or similar reagent to form a terephthalate ester.

In certain embodiments, the processes described herein further include continuously withdrawing a product stream containing terephthalic acid or an ester thereof from the rearrangement reaction zone. In certain embodiments, the process includes withdrawing a product stream containing terephthalic acid (or an ester or salt thereof) which also contains one or more co-products selected from benzene, benzoic acid (or esters or salts thereof), phthalic acid (or esters thereof), and isophthalic acid (or esters thereof). In certain embodiments, the process further includes a step of separating terephthalic acid (or esters thereof) from one or more of these co-products. In certain embodiments, the separating process includes one or more of distillation, and crystallization.

Polymer Compositions

In another aspect, provided are biobased monomers and polymer compositions derived therefrom.

In certain embodiments, provided are polymer compositions comprising isophthalic acid and esters thereof, characterized by their biobased carbon content. In certain embodiments, such compositions comprise compounds having a formula:

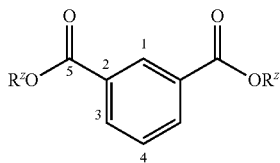

and characterized in that carbon atoms 1 through 5 are derived from biobased furfural. In certain embodiments of such compositions, $R^z$ is —H. In certain embodiments of such compositions, $R^z$ is $C_{1-20}$ aliphatic. In certain embodiments of such compositions $R^z$ is selected from the group consisting of: methyl, ethyl, n-butyl, and 2-ethylhexyl.

In certain embodiments, provided is biobased terephthalic acid compositions derived by rearrangement of such isophthalic acid compositions (or esters thereof).

In certain embodiments, such compositions comprise compounds having a formula:

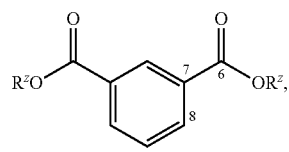

and characterized in that carbon atoms 6 through 8 are derived from a biobased alpha beta unsaturated acid. In certain embodiments of such compositions, $R^z$ is —H. In certain embodiments of such compositions, $R^z$ is $C_{1-20}$ aliphatic. In certain embodiments of such compositions, $R^z$ is selected from the group consisting of: methyl, ethyl, n-butyl, and 2ethylhexyl.

In certain embodiments, provided are biobased terephthalic acid compositions derived by rearrangement of such isophthalic acid compositions (or esters thereof).

In certain embodiments, provided are isophthalic acid compositions characterized in that five carbon atoms are derived from biobased furfural and the remaining three carbon atoms are derived from biobased acrylic acid. In certain embodiments, provided are biobased isophthalate esters derived from such isophthalic acid compositions. In certain embodiments, provided are biobased terephthalic acid compositions derived by rearrangement of such isophthalic acid compositions (or esters thereof).

In certain embodiments, provided are biobased polymers derived from the biobased isophthalic acid and terephthalic acid compositions described above. In certain embodiments, such polymers comprise polyesters. In certain embodiments, such polymers comprise polyamides.

In certain embodiments, provided are biobased polyester compositions comprising the biobased isophthalic acid and/or terephthalic acid compositions described above. In certain embodiments, such polyesters are the result of condensation of the acids (or esters thereof) with diols. In certain embodiments, the diol is a $C_{2-20}$ aliphatic diol. In certain embodiments, the diol is selected from the group consisting of: ethylene glycol, propylene glycol, 1,3-propanediol, 1,4 butanediol, and isosorbide. In certain embodiments, the diol is an aromatic diol. In certain embodiments, the diol is selected from the group consisting of: benzene dimethanol and bisphenol-A.

In certain embodiments, provided are biobased polyethylene terephthalate (PET) derived from the biobased terephthalic acid compositions described above. In certain embodiments, provided is biobased polytrimethylene terephthalate (PTT) derived from the biobased terephthalic acid compositions described above. In certain embodiments, provided is biobased polybutylene terephthalate (PBT) derived from the biobased terephthalic acid compositions described above.

In certain embodiments, provided is biobased polyethylene isophthalate (PEI) derived from the biobased isophthalic acid compositions described above. In certain embodiments, provided is biobased polytrimethylene isophthalate (PTI) derived from the biobased isophthalic acid compositions described above. In certain embodiments, provided is biobased polybutylene isophthalate (PBI) derived from the biobased isophthalic acid compositions described above.

In certain embodiments, provided is biobased polyethylene isophthalate derived from the biobased isophthalic acid compositions described above.

ENUMERATED EMBODIMENTS

The following enumerated embodiments/claims are representative of some aspects of the invention.

1. A compound having the formula:

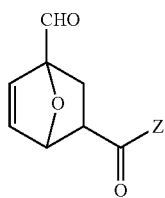

wherein Z is selected from the group consisting of —OR$^y$, —Cl, —Br, —NR$^y_2$, and —SR$^y$, where, where each R$^y$ is independently hydrogen, an optionally substituted group selected the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; where two R$^y$ on a nitrogen atom may be taken with the nitrogen atom to form an optionally substituted 4- to 7-membered heterocyclic ring having 0-2 additional heteroatoms independently selected from the group consisting of nitrogen, oxygen, and sulfur.

2. The compound of embodiment 1, wherein Z is —OR$^y$.

3. The compound of embodiment 2, wherein Z is —OH.

4. The compound of embodiment 3, wherein R$^y$ is C$_{1-20}$ aliphatic, or where R$^y$ is C$_{1-12}$ aliphatic, or where R$^y$ is C$_{1-8}$ aliphatic, or where R$^y$ is C$_{1-6}$ aliphatic, or where R$^y$ is C$_{1-4}$ aliphatic.

5. A method of making a compound of formula:

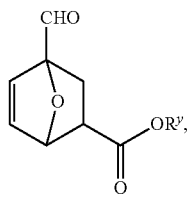

the method comprising the step of reacting furfural with an alpha beta unsaturated acid, where R$^y$ is independently hydrogen, or an optionally substituted moiety selected the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

5b. The method of embodiment 5, wherein the alpha beta unsaturated acid has the formula:

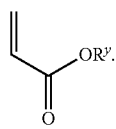

6. The method of embodiment 5, wherein R$^y$ is —H.

7. The method of embodiment 5, wherein R$^y$ is C$_{1-20}$ aliphatic, or where R$^y$ is C$_{1-12}$ aliphatic, or where R$^y$ is C$_{1-8}$ aliphatic, or where R$^y$ is C$_{1-6}$ aliphatic, or where R$^y$ is C$_{1-4}$ aliphatic.

8. A method for the production of a compound of formula:

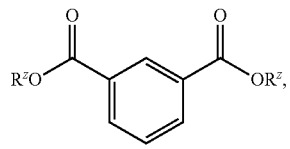

the method comprising the step of oxidizing a compound of formula:

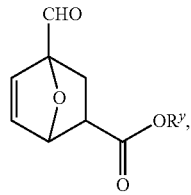

where each R$^z$ is independently selected from the group consisting of: —H, R$^y$, optionally substituted C$_{1-20}$ aliphatic, and optionally substituted aryl; and R$^y$ is independently hydrogen, or an optionally substituted moiety selected the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

9. The method of embodiment 8, wherein R$^z$ is —H.

10. The method of embodiment 8, wherein R$^z$ is —CH$_3$.

11. The method of embodiment 8, wherein the compound of formula:

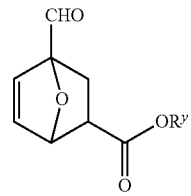

is produced by reaction of furfural with a compound having a formula:

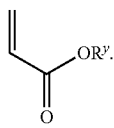

12. A isophthalic acid composition produced via cycloaddition reaction of furfural with an alpha beta unsaturated carboxylic acid.

13. The isophthalic acid composition of embodiment 12, characterized in that the isophthalic acid is at least partially derived from a biobased feedstock.
14. The isophthalic acid composition of embodiment 13, wherein carbon atoms one through five as shown in the formula:

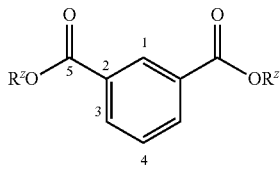

are derived from biobased furfural.
15. The isophthalic acid composition of embodiment 13, wherein carbon atoms six through eight as shown in the formula:

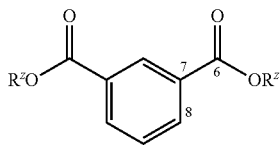

are derived from a biobased alpha beta unsaturated acid.
16. A biobased polymer composition derived from an isophthalic acid composition of any of embodiments 12 through 15.
17. The biobased polymer composition of embodiment 16, wherein the polymer comprises polyethylene isophthalate (PIT).
18. The biobased polymer composition of embodiment 17, wherein the polyethylene isophthalate further comprises biobased ethylene glycol.
19. A process for the production of biobased terephthalic acid or derivatives thereof, the method comprising the steps of:
    a) reacting ethylene oxide with carbon monoxide in one or more steps to provide a product selected from acrylic acid and acrylate ester;
    b) reacting the product of step (a) with furfural to provide a Diels Alder adduct;
    c) oxidizing the Diels Alder adduct of step (b) to provide product selected from isophthalic acid and isophthalate ester.
    d) treating the product of step (c) to convert the isophthalic acid to terephthalic acid.
20. The process of embodiment 19, wherein one or more steps are performed in a continuous process.
21. The process of embodiment 19, characterized in that at least one of the ethylene oxide, the carbon monoxide or the furfural is biobased.
22. A method of making a compound of formula:

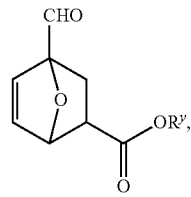

the method comprising the step of reacting furfural with beta propiolactone, where $R^y$ is independently hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.
23. The method of embodiment 22, wherein $R^y$ is —H.
24. The method of embodiment 22, wherein $R^y$ is $C_{1-20}$ aliphatic, or where $R^y$ is $C_{1-12}$ aliphatic, or where $R^y$ is $C_{1-8}$ aliphatic, or where $R^y$ is $C_{1-6}$ aliphatic, or where $R^y$ is $C_{1-4}$ aliphatic.
25. The method of embodiment 24, wherein the step of reacting is performed in the presence of a compound of formula $R^y$ OH.
26. A method for the production of a compound of formula

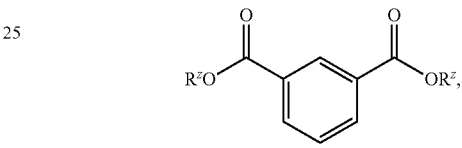

the method comprising the steps of reacting furfural with beta propiolactone and oxidizing the resulting adduct, where each $R^z$ is independently selected from the group consisting of:
    hydrogen, or an optionally substituted moiety selected the group consisting of acyl; arylalkyl; 6- to 10-membered aryl; $C_{1-20}$ aliphatic; 01-20 heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.
27. The method of embodiment 26, wherein $R^z$ is —H.
28. The method of embodiment 26, wherein $R^z$ is —CH3.
29. A method of making a compound of formula:

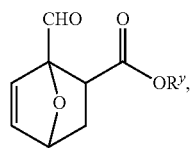

the method comprising the step of reacting furfural with beta propiolactone, where $R^y$ is independently hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

30. The method of embodiment 29, wherein $R^y$ is —H.

31. The method of embodiment 29, wherein $R^y$ is $C_{1-20}$ aliphatic, or where $R^y$ is $C_{1-12}$ aliphatic, or where $R^y$ is $C_{1-8}$ aliphatic, or where $R^y$ is $C_{1-6}$ aliphatic, or where $R^y$ is $C_{1-4}$ aliphatic.

32. A method for the production of a compound of formula:

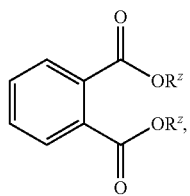

the method comprising the steps of reacting furfural with beta propiolactone and oxidizing the resulting adduct, where each $R^z$ is independently selected from the group consisting of:

hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group.

33. The method of embodiment 32, wherein $R^z$ is —H.

34. The method of embodiment 32, wherein $R^z$ is —CH3.

35. A process for the production of biobased terephthalic acid or derivatives thereof, the method comprising the steps of:

a) reacting ethylene oxide with carbon monoxide in one or more steps to provide beta propiolactone;
b) reacting the product of step (a) with furfural to provide an adduct selected from the group consisting of:

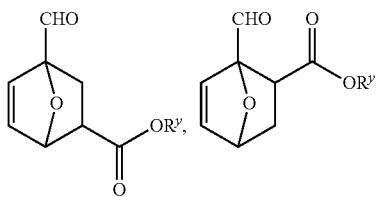

and mixtures of both of these;
c) oxidizing the adduct of step (b) to provide product selected from phthalic acid, phthalic acid ester, isophthalic acid and isophthalate ester.
d) treating the product of step (c) to convert the phthalic of isophthalic acid to terephthalic acid.

36. The process of embodiment 35, wherein one or more steps are performed in a continuous process.

37. The process of embodiment 35, characterized in that at least one of the ethylene oxide, the carbon monoxide or the furfural is biobased.

38. A method, comprising:
continuously feeding a first reaction zone with furfural and a compound of formula:

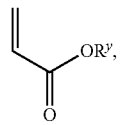

wherein $R^y$ is independently hydrogen, or an optionally substituted moiety selected the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10 membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group, to provide a first product stream comprising a first product formula:

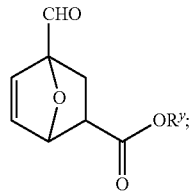

continuously feeding the first product stream to an oxidizing reaction zone where the first product is contacted with air to form a second product stream comprising a second product having formula:

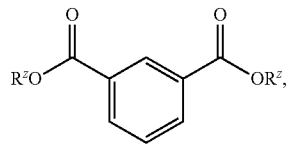

wherein each $R^z$ is independently selected from the group consisting of —H, $R^y$, optionally substituted $C_{1-20}$ aliphatic, and optionally substituted aryl; and continuously feeding the second product stream to a rearrangement reaction zone where the second product is converted to the compound of formula:

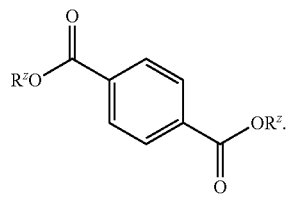

39. A method, comprising:
continuously feeding a first reaction zone with furfural and beta propiolactone, and optionally an alcohol of formula HOR$^y$, to provide a first product stream comprising a first product having formula:

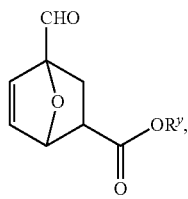

where R$^y$ is independently hydrogen, or an optionally substituted moiety selected the group consisting of acyl; arylalkyl; 6- to 10-membered aryl; C$_{1-20}$ aliphatic; C$_{1-20}$ heteroaliphatic having 1-4 heteroatoms independently selected from the group consisting of nitrogen, oxygen, and sulfur; 5- to 10 membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group; and;

continuously feeding the first product stream to an oxidizing reaction zone where the first product is contacted with air to form a second product stream comprising a second product having formula:

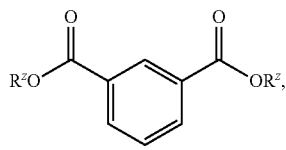

wherein each R$^z$ is independently selected from the group consisting of —H, R$^y$, optionally substituted C$_{1-20}$ aliphatic, and optionally substituted aryl; and continuously feeding the second product stream to a rearrangement reaction zone where the second product is converted to the compound of formula:

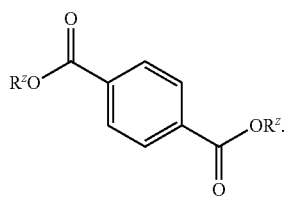

40. The method of embodiment 38 or 39, wherein R$^y$ is —H.
41. The method of embodiment 38 or 39, wherein R$^y$ is C$_{1-20}$ aliphatic.
42. The method of any one of embodiments 38 to 41, wherein R$^z$ is —H.
43. The method of any one of embodiments 38 to 41, wherein R$^z$ is —CH$_3$.
44. An isophthalic acid composition produced via cycloaddition reaction of furfural with an alpha beta unsaturated carboxylic acid, wherein the isophthalic acid is at least partially derived from a biobased feedstock.

45. An isophthalic acid composition produced via reaction of furfural with beta propiolactone, wherein the isophthalic acid is at least partially derived from a biobased feedstock.
46. The isophthalic acid composition of embodiment 44 or 45, wherein carbon atoms one through five as shown in the formula:

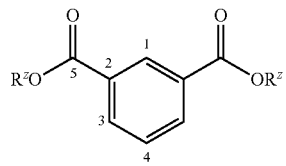

are derived from biobased furfural.
47. The isophthalic acid composition of embodiment 44, wherein carbon atoms six through eight as shown in the formula:

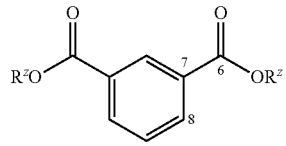

are derived from a biobased alpha beta unsaturated acid.
48. The isophthalic acid composition of embodiment 45, wherein carbon atoms six through eight as shown in the formula:

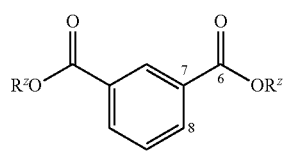

are derived from a biobased beta propiolactone.
49. A biobased polymer composition derived from an isophthalic acid composition of any one of embodiments 44 to 48.
50. The biobased polymer composition of embodiment 49, wherein the polymer comprises polyethylene isophthalate (PIT).
51. The biobased polymer composition of embodiment 50, wherein the polyethylene isophthalate further comprises biobased ethylene glycol.
52. A method for the production of biobased terephthalic acid, comprising:
a) reacting ethylene oxide with carbon monoxide to provide a product selected from beta propiolactone, acrylic acid and acrylate ester;
b) reacting the product of step (a) with furfural to provide a Diels Alder adduct;
c) oxidizing the Diels Alder adduct of step (b) to provide product selected from isophthalic acid and isophthalate ester; and
d) treating the product of (c) to convert the isophthalic acid to terephthalic acid.
53. The method of embodiment 52, wherein one or more steps are performed in a continuous process.
54. The method of embodiment 52 or 53, wherein at least one of the ethylene oxide, the carbon monoxide or the furfural is biobased.

What is claimed is:

1. A method, comprising:

continuously feeding a first reaction zone with furfural and a compound of formula:

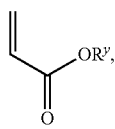

wherein $R^y$ is independently hydrogen, or an optionally substituted moiety selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group, to provide a first product stream comprising a first product of formula:

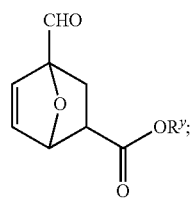

continuously feeding the first product stream to an oxidizing reaction zone where the first product is contacted with air to form a second product stream comprising a second product having formula:

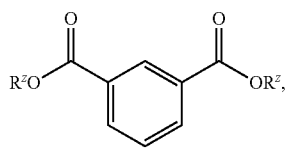

wherein each $R^z$ is independently selected from the group consisting of —H, $R^y$, optionally substituted $C_{1-20}$ aliphatic, and optionally substituted aryl; and continuously feeding the second product stream to a rearrangement reaction zone where the second product is converted to a compound of formula:

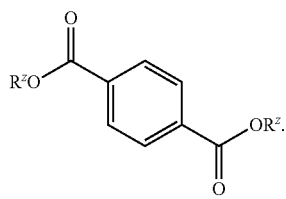

2. A method, comprising:

continuously feeding a first reaction zone with furfural and beta propiolactone, and an alcohol of formula $HOR^y$, to provide a first product stream comprising a first product having formula:

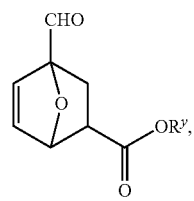

wherein $R^y$ is independently hydrogen, or an optionally substituted moiety selected from the group consisting of acyl; arylalkyl; 6- to 10-membered aryl; $C_{1-20}$ aliphatic; $C_{1-20}$ heteroaliphatic having 1-4 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; and an oxygen protecting group; and; continuously feeding the first product stream to an oxidizing reaction zone where the first product is contacted with air to form a second product stream comprising a second product having formula:

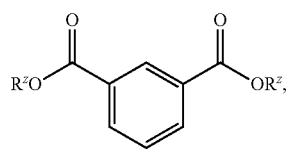

wherein each $R^z$ is independently selected from the group consisting of —H, $R^y$, optionally substituted $C_{1-20}$ aliphatic, and optionally substituted aryl; and continuously feeding the second product stream to a rearrangement reaction zone where the second product is converted to a compound of formula:

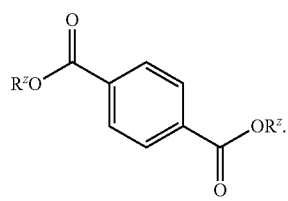

3. The method of claim 1 or 2, wherein $R^y$ is —H.

4. The method of claim 1 or 2, wherein $R^y$ is $C_{1-20}$ aliphatic.

5. The method of claim 1, wherein each $R^z$ is —H.

6. The method of claim 1, wherein each $R^z$ is —$CH_3$.

7. A method for the production of biobased terephthalic acid or an ester thereof comprising:

a) reacting ethylene oxide with carbon monoxide to provide a product selected from beta propiolactone, acrylic acid and acrylate ester;

b) reacting the product of step (a) with furfural to provide a Diels Alder adduct;
c) oxidizing the Diels Alder adduct of step (b) to provide a product selected from isophthalic acid and isophthalate ester; and
d) treating the product of (c) to convert the isophthalic acid to terephthalic acid or the isophthalate ester to a terephthalate ester.

8. The method of claim 7, wherein one or more steps are performed in a continuous process.

9. The method of claim 7 or 8, wherein at least one of the ethylene oxide, the carbon monoxide or the furfural is biobased.

\* \* \* \* \*